US012334192B2

(12) United States Patent
Singal et al.

(10) Patent No.: US 12,334,192 B2
(45) Date of Patent: *Jun. 17, 2025

(54) COMPUTER-IMPLEMENTED SYSTEM AND METHOD FOR IDENTIFYING SIMILAR PATIENTS

(71) Applicant: FOUNDATION MEDICINE, INC., Cambridge, MA (US)

(72) Inventors: Gaurav Singal, Cambridge, MA (US); Mary Patricia Lancelotta, Somerville, MA (US)

(73) Assignee: Foundation Medicine, Inc., Boston, MA (US)

( * ) Notice: Subject to any disclaimer, the term of this patent is extended or adjusted under 35 U.S.C. 154(b) by 1492 days.

This patent is subject to a terminal disclaimer.

(21) Appl. No.: 16/579,508

(22) Filed: Sep. 23, 2019

(65) Prior Publication Data

US 2020/0020452 A1  Jan. 16, 2020

Related U.S. Application Data

(63) Continuation of application No. 14/972,715, filed on Dec. 17, 2015, which is a continuation-in-part of application No. 14/463,068, filed on Aug. 19, 2014, which is a continuation-in-part of application No. 14/146,743, filed on Jan. 3, 2014, said application No. 14/972,715 is a continuation-in-part of application No. 14/146,743, filed on Jan. 3, 2014.

(60) Provisional application No. 62/093,397, filed on Dec. 17, 2014, provisional application No. 61/749,288, filed on Jan. 5, 2013, provisional application No. 61/749,291, filed on Jan. 5, 2013.

(51) Int. Cl.

| G16B 50/00 | (2019.01) |
| G06F 16/245 | (2019.01) |
| G06F 16/901 | (2019.01) |
| G16B 50/30 | (2019.01) |
| G16H 10/60 | (2018.01) |
| G16H 15/00 | (2018.01) |
| G16H 50/20 | (2018.01) |
| G16H 50/70 | (2018.01) |
| G16H 70/60 | (2018.01) |
| G16H 80/00 | (2018.01) |

(52) U.S. Cl.
CPC .......... *G16B 50/00* (2019.02); *G06F 16/245* (2019.01); *G06F 16/9024* (2019.01); *G16B 50/30* (2019.02); *G16H 10/60* (2018.01); *G16H 50/20* (2018.01); *G16H 50/70* (2018.01); *G16H 70/60* (2018.01); *G16H 80/00* (2018.01); *G16H 15/00* (2018.01)

(58) Field of Classification Search
None
See application file for complete search history.

(56) References Cited

U.S. PATENT DOCUMENTS

| 6,458,080 | B1 | 10/2002 | Brown et al. |
| 6,527,712 | B1 | 3/2003 | Brown et al. |
| 7,024,369 | B1 | 4/2006 | Brown et al. |
| 7,353,238 | B1 | 4/2008 | Gliklich |
| 10,885,807 | B1 | 1/2021 | Lavi et al. |
| 11,158,425 | B2 | 10/2021 | de Deus et al. |
| 11,450,438 | B2 | 9/2022 | Pellini et al. |
| 11,896,596 | B2 | 2/2024 | Paik et al. |
| 12,087,453 | B2 | 9/2024 | Pellini et al. |
| 2002/0052761 | A1 | 5/2002 | Fey et al. |
| 2003/0046114 | A1 | 3/2003 | Davies et al. |
| 2003/0113756 | A1 | 6/2003 | Mertz |
| 2004/0078236 | A1 | 4/2004 | Stoodley et al. |
| 2005/0026117 | A1 | 2/2005 | Judson et al. |
| 2005/0261941 | A1 | 11/2005 | Scarlat |
| 2006/0004526 | A1 | 1/2006 | Hadd et al. |
| 2008/0161661 | A1 | 7/2008 | Gizewski |
| 2008/0201172 | A1 | 8/2008 | McNamar |
| 2009/0080734 | A1 | 3/2009 | Moriya et al. |

(Continued)

FOREIGN PATENT DOCUMENTS

| KR | 20110097889 A | 8/2011 |
| WO | WO-2012059839 A2 | 6/2012 |
| WO | WO-2014107549 A2 | 7/2014 |

OTHER PUBLICATIONS

[No Author Listed] "Graph Database—Wikipedia" Dec. 7, 2014; Retrieved from the internet on Jun. 26, 2018; en.wikipedia.org/w/index.php?title=Graph_database&oldid=637006716, 5 pages.

(Continued)

*Primary Examiner* — Joseph Woitach
(74) *Attorney, Agent, or Firm* — MORRISON & FOERSTER LLP

(57) ABSTRACT

A computer system includes a database of pathology information for a plurality of patients including at least one current patient; a memory; and a processor configured to identify the at least one second practitioner based on a similarity between the patient-specific pathology of the at least one current patient and the similar patient of the at least one second practitioner; display an indication to the first practitioner that the at least one second practitioner has been identified while keeping the identity of the at least one second practitioner and the similar patient confidential; present the first practitioner with a control to communicate with the at least one second practitioner; receive, from the at least one second practitioner, discrete responses to questions regarding the similar patient; and determine, based on the discrete responses, a recommendation of a treatment for the at least one current patient.

19 Claims, 15 Drawing Sheets

(56) References Cited

U.S. PATENT DOCUMENTS

| | | |
|---|---|---|
| 2009/0222286 A1 | 9/2009 | Elsholz |
| 2009/0287503 A1 | 11/2009 | Angell et al. |
| 2010/0070293 A1 | 3/2010 | Brown et al. |
| 2010/0125462 A1 | 5/2010 | Aggarwal |
| 2010/0131293 A1 | 5/2010 | Linthicum et al. |
| 2010/0138199 A1 | 6/2010 | Soto et al. |
| 2010/0191100 A1 | 7/2010 | Anderson et al. |
| 2010/0198619 A1 | 8/2010 | Whelchel et al. |
| 2010/0218132 A1 | 8/2010 | Soni et al. |
| 2011/0112860 A1 | 5/2011 | Kehr |
| 2011/0276347 A1 | 11/2011 | Dalton |
| 2012/0041683 A1 | 2/2012 | Vaske et al. |
| 2012/0157340 A1 | 6/2012 | Cesano et al. |
| 2013/0096948 A1 | 4/2013 | Parkinson et al. |
| 2013/0226612 A1 | 8/2013 | Carmeli et al. |
| 2014/0336943 A1 | 11/2014 | Pellini et al. |
| 2014/0337052 A1 | 11/2014 | Pellini et al. |
| 2015/0046180 A1 | 2/2015 | de Deus et al. |
| 2015/0046191 A1 | 2/2015 | de Deus et al. |
| 2015/0100341 A1 | 4/2015 | Pecora |
| 2015/0112705 A1 | 4/2015 | Neville |
| 2015/0127385 A1 | 5/2015 | Pecora |
| 2016/0103973 A1 | 4/2016 | Singal et al. |
| 2016/0270717 A1 | 9/2016 | Luna et al. |
| 2016/0350491 A1 | 12/2016 | Pecora |
| 2016/0350492 A1 | 12/2016 | Pecora |
| 2016/0350495 A1 | 12/2016 | Pecora |
| 2017/0076046 A1 | 3/2017 | Barnes et al. |
| 2017/0365182 A1 | 12/2017 | Lavi et al. |
| 2018/0174688 A1 | 6/2018 | Pecora |
| 2019/0172584 A1 | 6/2019 | Athey et al. |
| 2019/0392924 A1 | 12/2019 | Bettencourt-Silva et al. |
| 2020/0020430 A1 | 1/2020 | de Deus et al. |
| 2020/0211679 A1 | 7/2020 | Pellini et al. |
| 2020/0258601 A1 | 8/2020 | Lau |
| 2020/0294668 A1 | 9/2020 | Pellini et al. |
| 2021/0090694 A1 | 3/2021 | Colley et al. |
| 2021/0233664 A1 | 7/2021 | Colley et al. |
| 2022/0399131 A1 | 12/2022 | Pellini et al. |

OTHER PUBLICATIONS

Barabasi et al "Network medicine: a network-based approach to human disease" Nature Reviews Genetics (2011) vol. 12 No. 1 pp. 56-68.

Bebek et al, "Network biology methods integrating biological data for translational science" Briefings in Bioinformatics (2012) vol. 13, No. 4 pp. 446-459.

Chun et al., "A network perspective on unraveling the role of TRP channels in biology and disease" Pflugers Archiv—European Journal of Physiology (2014) vol. 446 No. 2 pp. 173-182.

Haga et al., "Developing patient-friendly genetic and genomic test reports formats to promote patient engagement and understanding" genome Medicine (2014) vol. 6 No. 58 pp. 1-11.

Yilmaz et al., (2009). "Gene-disease relationship discovery based on model-driven data integration and database view definition," Bioinformatics, 25(2):230-236.

Extended European Search Report and Opinion received for European Patent Application No. 14735224.9 mailed Jul. 14, 2016, 8 pages.

Extended European Search Report and Opinion received for European Application No. 15833420.1 mailed Mar. 2, 2018, 12 pages.

Extended European Search Report and Opinion received for European Application No. 15871055.8 completed Jul. 3, 2018, 11 pages.

Extended European Search Report and Opinion received for European Application No. 20201144.1 mailed Mar. 30, 2021, 11 pages.

International Search Report received for International Patent Application No. PCT/US2014/010124 mailed May 8, 2014, 3 pages.

International Search Report received for International Patent Application No. PCT/US2014/010125 mailed Jun. 24, 2014, 5 pages.

International Search Report received for International Patent Application No. PCT/US2015/045859 mailed Nov. 24, 2015, 4 pages.

International Search Report received for International Patent Application No. PCT/US2015/066325 mailed Apr. 7, 2016, 3 pages.

Written Opinion of the International Searching Authority for PCT/US2015/045859 mailed Nov. 24, 2015, 11 pages.

Written Opinion of the International Searching Authority for PCT/US2015/066325 mailed Apr. 7, 2016, 6 pages.

FIG. 13

COMPUTER-IMPLEMENTED SYSTEM AND METHOD FOR IDENTIFYING SIMILAR PATIENTS

RELATED APPLICATIONS

This application is a continuation of U.S. application Ser. No. 14/972,715, filed Dec. 17, 2015, which claims priority under 35 U.S.C. § 119 (e) to U.S. Provisional Application Ser. No. 62/093,397 entitled "COMPUTER-IMPLEMENTED SYSTEM AND METHOD FOR IDENTIFYING SIMILAR PATIENTS," filed Dec. 17, 2014, which application is herein incorporated by reference in its entirety. The Ser. No. 14/972,715 application is a continuation-in-part of U.S. patent application Ser. No. 14/463,068 entitled "SYSTEM AND METHOD FOR MANAGING GENOMIC INFORMATION" filed Aug. 19, 2014, which claims priority under 35 U.S.C. § 119 (e) to U.S. Provisional App. No. 61/749,291, entitled "SYSTEM AND METHOD FOR MANAGING GENOMIC TESTING RESULTS," filed Jan. 5, 2013, and U.S. Provisional App. No. 61/749,288, entitled "SYSTEM AND METHOD FOR OUTCOME TRACKING AND ANALYSIS," filed Jan. 5, 2013. The Ser. No. 14/972,715 application is also a continuation-in-part of U.S. application Ser. No. 14/146,743, entitled SYSTEM AND METHOD FOR MANAGING GENOMIC TESTING RESULTS, filed Jan. 3, 2014 which is a non-provisional application of and claims priority under 35 U.S.C. § 119 (e) to U.S. Provisional App. No. 61/749,291, entitled "SYSTEM AND METHOD FOR MANAGING GENOMIC TESTING RESULTS," filed Jan. 5, 2013, and U.S. Provisional App. No. 61/749,288, entitled "SYSTEM AND METHOD FOR OUTCOME TRACKING AND ANALYSIS," filed Jan. 5, 2013, of which applications are incorporated herein by reference by their entirety.

BACKGROUND

Genomic testing of cancer cells shows significant promise towards developing better understanding of cancers and managing more effective treatment approaches. Genomic testing involves the sequencing of the genome of a patient's cancer cells and identifying any genomic alteration in those cells. A genomic alteration can include, for example, mutations, deleted gene sequences, amplifications, translocation, among other options. Understanding these genomic alterations as they are found in a specific patient's cancer may also help develop better treatments and help identify the best approaches for treating specific cancer variants using genomic information.

SUMMARY

It is realized that the adoption and integration of genomic testing into daily practice faces significant hurdles, in part, based on the ability to access and the volume of the information that needs to be reviewed and understood in order to facilitate treatment decisions. Further, the complexity of the genomic analysis has also limited its potential and in some cases limited implementation. It is also realized that conventional approaches for providing genomic alteration information are not readily appreciated by the majority of practitioners (e.g., physicians, oncologists, etc.) for their diagnostic value. Nor can the majority of practitioners incorporate such information into actionable steps to be taken with a given patient, or identify clinically relevant information. Interpreting genomic data is further complicated by the sparsity of some genomic findings and the associated scarcity of public data regarding the efficacy of treatments targeted against those findings, especially when stratified by tumor type.

According to one aspect of the present invention, it is realized that new tools that permit a practitioners such as physicians to more easily locate other physicians that have successfully treated similar patients would be beneficial to their practice. Further, tools that permit identification of successful treatments for specific genomic alterations in a particular cancer type determined from a current patient would also increase the likelihood that the patient could be successfully treated. To this end, a system may be provided that permits the user to locate similar patients using genomic information related to a patient's cancer. For instance, information relating to genetic alterations and the patient's tumor type may be used to identify similar patients within a database. Preferably, such information may be used to locate similar patients where treatment was successful or had some other positive outcome.

According to other aspects, curated information is provided on the system to enable physicians to make informed decisions regarding the implications of the presence of specific genomic alterations. Curated information includes interpretations of available information (e.g., existing therapies, clinical trials, journals, and publications) for genomic alterations that may be found in a patient's tumor as a result of the genomic analysis. The genomic analysis can identify, for example, a tumor type, an affected gene, and an alteration type specific to a given patient and their cancer. The available information that can be curated can be associated with, and organized by, any of the information provided in the genomic analysis (e.g., specific to tumor type, gene, and alteration). Such information may be stored in a database and accessed by physicians though one or more user interfaces.

Conventional interfaces such as databases are not generally capable of matching patient information. For instance, much of the data stored in such systems is generally sparse, and it is very difficult to determine, through manual searching, all of the information and relevant patient data that might be applicable to a particular patient. According to one aspect of the present invention, an ability is provided for searching a centralized database of genomic information collected on a number of patients, and performing a matching process by which similar patients may be discovered. Further, tools may be provided that permit practitioners such as physicians to contact other physicians that have treated the identified similar patients. Because such a tool is provided, it allows for fast identification of similar patient scenarios, and increases the ability of the physician to solicit information regarding treatment.

According to another aspect of the present invention, the communication permits patients to be matched and identified without revealing their identities to other physician users. However, according to one aspect, physicians are provided a facility for communicating between physicians while not revealing contact information such that the identification of physicians with matching patients is kept confidential. Both the initial communication and responses to the inquiry may be stored within the database and associated with the particular patient and/or cancer type. After a particular communication between physicians occurs, this information may be stored in the database and accessed for future use (e.g., by another physician searching for a similar patient having a similar cancer). By providing such communication capabilities, a physician or other health care provider may more easily locate the best treatment information in a timely manner.

According to another aspect of the present invention, a communication system is provided that allows physician users to discuss cases in a semi-structured manner. For instance, some questions are provided in a structured format where discrete responses are provided (e.g., best response, duration, etc.). Some questions are unstructured that permit other physician users to convey a larger clinical narrative (e.g., via any additional comments field, via questions such as "Why was the patient not treated with a therapy?" among others). By providing some structured data, responses may be aggregated from among physician providers and reused by the system. In one example implementation, structured data responses from multiple providers may be aggregated and provided to a physician user within an interface. In one embodiment, such information may be presented to a physician user within a matrix of results. Such information may include, for example, de-identified information regarding similar patients identified through a matching process. The presented information may also include genomic information as well as the response information collected from other physician users.

According to another aspect of the present invention, is appreciated that patient context information may be used to perform a matching process for identifying similar patients. As used herein, patient context information includes information that describes a state of a particular patient with respect to his/her disease state, along with the generic state of the disease. In one embodiment, patient context information may include disease phenotype and genetic alterations. According to one aspect of the present invention, it is realized that disease subtypes can be arranged in disease groups depending on the clinical and functional similarity of the diseases. Such disease subtypes (e.g., tumor types) can be grouped according to expert information, creating disease ontology groups (DOGs). In a similar manner, alterations may be grouped into alteration groups that are functionally similar. Disease ontology groups (DOGs) and alteration groups (AGs) can be used to locate similar patients. In particular, similar patients may be defined as those having the same disease type (or another disease type in the same DOG) and having an alteration that falls within the same alteration group (AG).

In one aspect of the present invention, it is appreciated that treatment data may be very sparse, such that an exact match based on a specific information may not yield any result. However, it is appreciated that diseases may be clinically similar such that patients and their outcome data for similar diseases may be grouped or pooled together, such that a search result may be determined. Also, it is appreciated that alteration data can be generalized and therefore patient data and associated outcome data may be grouped together for the purpose of performing a similarity search.

Once one or more similar patients are identified, a physician may be permitted (e.g., via a communication tool presented within a user interface) to contact another physician who treated or is treating the identified similar patient. In one embodiment, patient data is anonymized and only the physician contact information is provided, if offered by the responding physician. However, the communication facility may be capable of indicating to the responding physician which similar patient triggered the communication so that the responding physician may respond appropriately.

Further, after physicians are identified as having similar patients, the physician may be contacted by the computer system to request information about how they treated those patients and/or to share their experiences. As these physicians respond to these requests, the requests and associated responses may be stored within a database. This database of communications between physicians may be used for future treatment information that can be presented to other physicians responsive to future queries (e.g., other patient matching instances).

There may be several communication instances that provide additional functionality, such as initiating contact with another physician based on a single patient per request, even though it may be many similar patients that are matched. According to one aspect, it is appreciated that a physician might be overwhelmed when requested information regarding multiple patients. Thus, according to one embodiment, the most relevant patient that matches the patient currently being treated is presented to the physician. Also, it is appreciated that if a physician has already responded to a similar request but there are multiple matching patients, information that has already been stored within the database may be presented, however, the system may also prompt the physician about other patients so that the database may be improved. In another example patient, the physician has entered a response more than a predetermined amount of time, is appreciated that the patient's treatment course may have changed, and the physician may be prompted to provide updated information. Other embodiments of the present invention relate to the interface used to communicate with physicians and to encourage their engagement with other physicians and the system.

According to one aspect of the present invention, a distributed computer system is provided comprising a database including patient-specific pathology information relating to a plurality of patients including at least one current patient, an interface for a practitioner that provides treatment for the at least one current patient, and a matching component adapted to identify a similar patient among the plurality of patients based on a similarity between the patient-specific pathology information and patient-specific pathology information of the similar patient. In one embodiment of the present invention, the patient-specific pathology information relating to the patient includes at least one of a group comprising disease phenotype information and genetic alteration information.

In another embodiment, the disease phenotype information is arranged into one or more disease ontology groups, and wherein the matching component is adapted to locate the similar patient based on the one or more disease ontology groups. In another embodiment, the genetic alteration information is arranged into one or more alteration groups, and wherein the matching component is adapted to locate the similar patient based on the one or more alteration groups. In another embodiment, the interface for a practitioner is adapted to display an indication to the practitioner that the similar patient is identified.

In another embodiment, the system further comprises a communication component that permits the practitioner to communicate with a treating practitioner related to the identified similar patient. In another embodiment, the system is adapted to identify other practitioners that have selected to communicate about their patients. In another embodiment, the system identifies other practitioners that have been selected to communicate about their patients.

In another embodiment, the communication component includes an interface that accepts structured data from at least one of the other practitioners. In another embodiment, the communication component includes an interface that accepts response data from at least one of the other practitioners. In another embodiment, the response data includes structured and unstructured data.

In another embodiment, the communication component includes an interface presents response data in a matrix of results. In another embodiment, the matrix includes de-identified information relating to the identified similar patient. In another embodiment, the matrix includes genomic data and associated response data. In another embodiment, the system includes a component that aggregates structured data among a plurality of identified similar patients and an interface that presents the aggregated structured data to the practitioner.

In another embodiment, the system is adapted to collect biomarker data and is adapted to store the biomarker data in the database. In another embodiment, the database is adapted to store the patient-specific pathology information and biomarker data within a graph-based data structure. In another embodiment, the database is adapted to store information organized into a plurality of tuples of information. In another embodiment, each of the plurality of tuples of information includes at least two elements connected by a relation. In another embodiment, the system includes a component adapted to determine one or more actionable items within the graph-based data structure responsive to the biomarker data and patient-specific pathology information. In another embodiment, the plurality of tuples is organized by the system into a walkable graph representation.

According to another aspect of the present invention, a method is provided comprising acts of storing, in a database, patient-specific pathology information relating to a plurality of patients including at least one current patient, presenting, to a practitioner, a computer-based interface of a distributed computer system, the practitioner providing treatment for the at least one current patient, and identifying, by the distributed computer system, a similar patient among the plurality of patients responsive to an act of determining a similarity between the patient-specific pathology information and patient-specific pathology information of the similar patient. In one embodiment of the present invention, the patient-specific pathology information relating to the patient includes at least one of a group comprising disease phenotype information and genetic alteration information.

In another embodiment of the present invention, the disease phenotype information is arranged into one or more disease ontology groups, and wherein the matching component is adapted to locate the similar patient based on the one or more disease ontology groups. In another embodiment, the method further comprises an act of arranging genetic alteration information into one or more alteration groups, and wherein the method further comprises locating the similar patient based on the one or more alteration groups.

In another embodiment, the method further comprises an act of displaying, in the interface to the practitioner, an indication that the similar patient is identified. In another embodiment, the method further comprises an act of permitting the practitioner to communicate with a treating practitioner related to the identified similar patient. In another embodiment, the method further comprises an act of identifying, by the computer system, other practitioners that have selected to communicate about their patients. In another embodiment, the method further comprises an act of identifying, by the computer system, other practitioners that have been selected to communicate about their patients.

In another embodiment, the method further comprises an act of accepting, from at least one of the other practitioners within an interface of the computer system, response data that includes structured data. In another embodiment, the method further comprises an act of accepting, from at least one of the other practitioners within an interface of the computer system, response data. In another embodiment, the response data includes structured and unstructured data. In another embodiment, the method further comprises an act of presenting, within an interface of the computer system, response data in a matrix of results. In another embodiment, the matrix includes de-identified information relating to the identified similar patient. In another embodiment, the matrix includes genomic data and associated response data. In another embodiment, the method further comprises an act of aggregating, by the computer system, structured data among a plurality of identified similar patients and presenting, within an interface of the computer system, the aggregated structured data to the practitioner. In another embodiment, method further comprises an act of collecting biomarker data and storing the biomarker data in the database.

In another embodiment, the method further comprises an act of storing the patient-specific pathology information and biomarker data within a graph-based data structure. In another embodiment, the method further comprises an act of organizing the patient-specific pathology information and biomarker data into a plurality of tuples of information. In another embodiment, each of the plurality of tuples of information includes at least two elements connected by a relation. In another embodiment, the method further comprises an act of determining one or more actionable items within the graph-based data structure responsive to the biomarker data and patient-specific pathology information. In another embodiment, the plurality of tuples are organized by the system into a walkable graph representation.

Still other aspects, examples, and advantages of these exemplary aspects and examples, are discussed in detail below. Moreover, it is to be understood that both the foregoing information and the following detailed description are merely illustrative examples of various aspects and examples, and are intended to provide an overview or framework for understanding the nature and character of the claimed aspects and examples. Any example disclosed herein may be combined with any other example in any manner consistent with at least one of the objects, aims, and needs disclosed herein, and references to "an example," "some examples," "an alternate example," "various examples," "one example," "at least one example," " this and other examples" or the like are not necessarily mutually exclusive and are intended to indicate that a particular feature, structure, or characteristic described in connection with the example may be included in at least one example. The appearances of such terms herein are not necessarily all referring to the same example.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of a particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. In the figures:

FIG. 13 illustrates yet another example of a user interface displaying a feedback view according to various aspects of the present invention.

DETAILED DESCRIPTION

As described above, genomic testing provides unique opportunities to make more informed treatment decisions, especially in the field of cancer diagnosis and therapy development. Some conventional approaches can fail to provide useable information within the volumes of information provided as results of genomic testing. Further, it is appreciated that some conventional approaches fail to focus practitioners on actionable information within the genomic testing information and any associated treatment information.

Accordingly, provided are systems and methods for managing genomic testing information and providing a capability for identifying similar patients for the purpose of allowing physicians and other practitioners the ability to exchange information to improve the quality of treatment.

Figure 1:
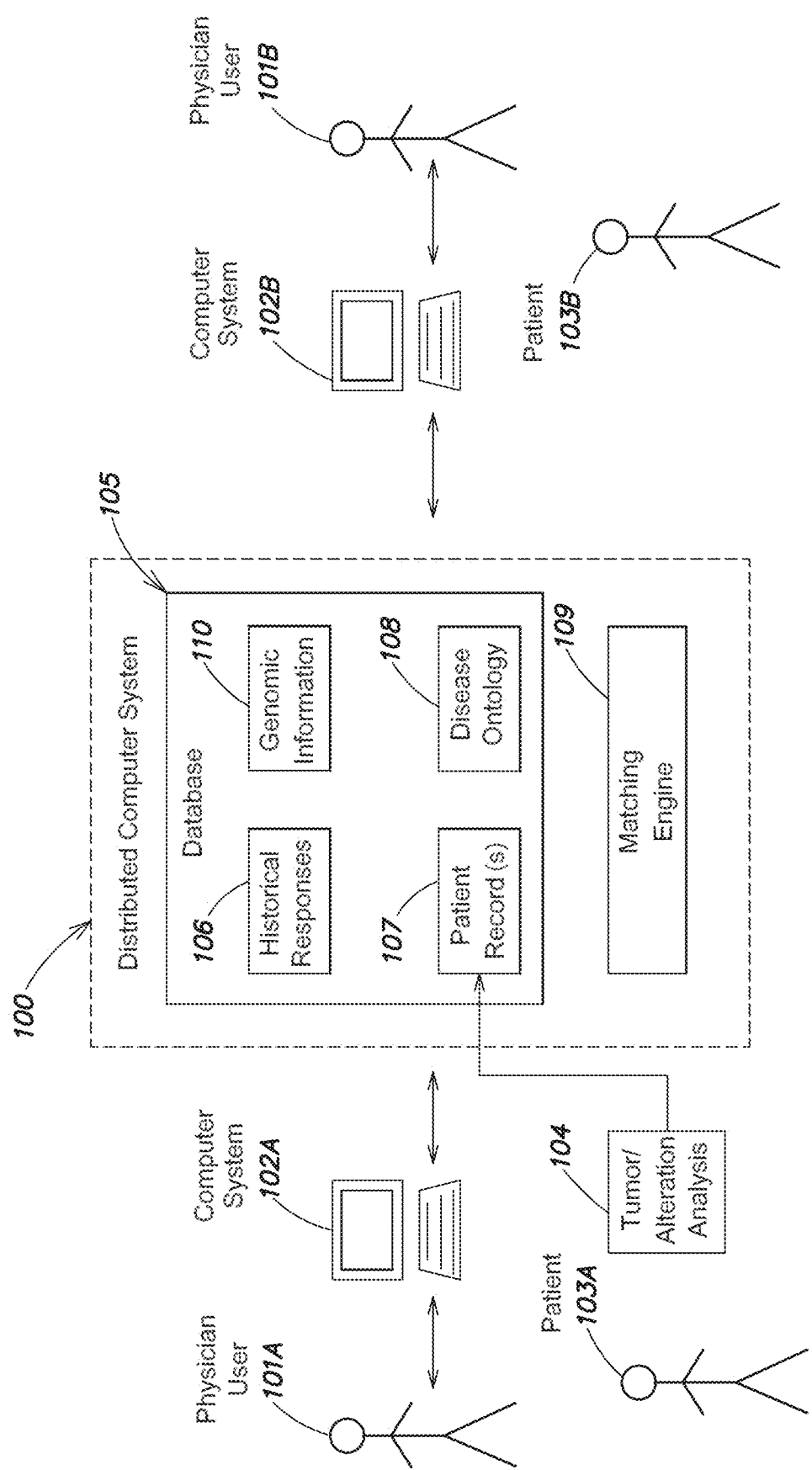
FIG. 1 is a block diagram showing a system for identifying similar patients according to various aspects of the present invention.

One or more aspects of the present invention may be implemented using a distributed computer system 100 is shown in FIG. 1. System 100 may include one or more client systems (e.g., computer system 102A, computer system 102B) through which one or more practitioners (e.g., physician user 102A, physician user 102B) interface to the system. As discussed, a particular physician may desire to determine treatment options for a particular patient (e.g., patient 103A).

In one embodiment, a patient's tumor and is analyzed and stored as part of a patient record (e.g., as part of patient record(s) 107 within a database 105). The information may include, for example, a tumor type, alteration information, outcome information, treatment information, among other information. Further, system 100 may store disease ontology information 108 that describes information identifying various diseases. In one embodiment, such diseases may include different types of cancers. In another embodiment, it is appreciated that some types of cancers are similar and therefore they may be grouped for the purpose of identifying patients with similar disease states.

Further, system 100 may include a database of genomic information 110, including, but not limited to, alteration data including grouping information that associates related alterations. Genomic information 110 may include other information, such as for example, gene information, gene associations, gene states, therapies for particular genetic states and know effects of such therapies, among other related information.

In one embodiment, system 100 may include a matching engine that determines one or more similar patients as compared to a current patient being analyzed. For instance, system 100 may be capable of communicating and receiving information regarding a number of patients (e.g., patients 103A, 103B) as received from multiple sources. System 100 may be adapted to communicate with other physicians (e.g., physician 101B) that treat other patients (e.g., patient 103B). System 100 and its matching engine may identify other patients (e.g., patient 103B) who are similar to a current patient (e.g., patient 103A). After identifying one or more similar patients, system 100 may be capable of facilitating communication between treating physicians associated with the matched patients (e.g., patient 103A, patient 103B).

In one example implementation, patient context information may be used to perform a matching process for identifying similar patients. In one embodiment, patient context information may include disease phenotype and genetic alterations. As discussed, it is realized that disease subtypes can be arranged in disease groups depending on the clinical and functional similarity of the diseases. Such disease subtypes (e.g., tumor types) can be grouped according to expert information, creating disease ontology groups (DOGs). In a similar manner, alterations may be grouped into alteration groups that are functionally similar. Disease ontology groups (DOGs) and alteration groups (AGs) can be used to locate similar patients. In particular, similar patients may be defined as those having the same disease type (or another disease type in the same DOG) and having an alteration that falls within the same alteration group (AG).

Figure 2:
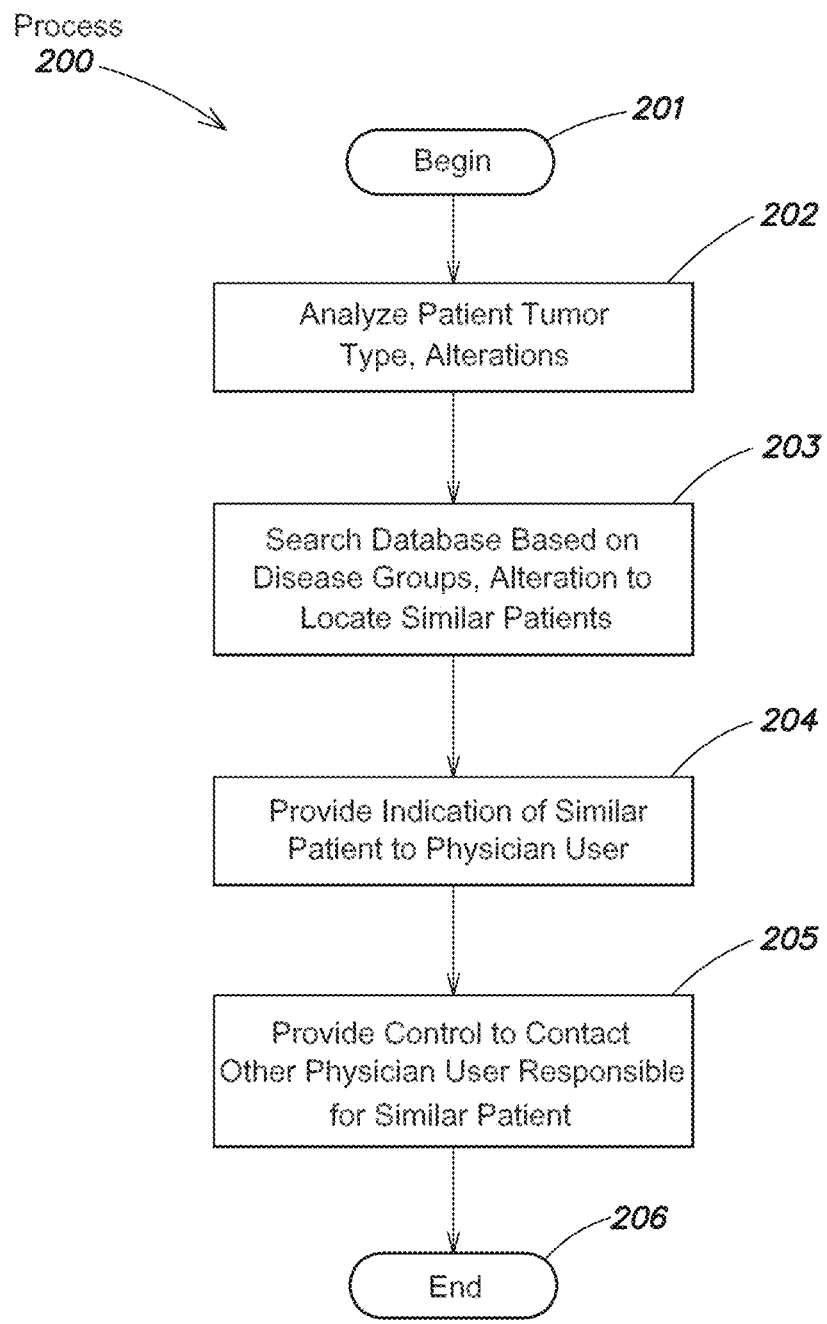
FIG. 2 shows an example process for identifying similar patients according to one embodiment of the present invention.

FIG. 2 shows an example process 200 for identifying similar patients according to one embodiment of the present invention. At block 201, process 200 begins. At block 202, the patient's particular cancer is analyzed to determine one or more generic alterations present within that cancer. As discussed, one aspect of the invention relates to obtaining a physical sample of a patient's tumor and performing an analysis of the tumor with the objective of determining a customized treatment for that particular patient. Such alteration and tumor type information may be entered into a database that includes patient information, and such information may be used to perform a matching function to determine similar patients.

At block 203, the system searches the database to locate similar patients. In one embodiment, the system searches the database of patients based on disease and alteration information, and incorporating groupings of the disease and alteration information. As discussed, in a sparse database, a direct match of a patient may not be available and/or fully indicative of similarity. In one implementation, disease groups of similar disease types and alteration groups of similar alterations may be used to locate similar patients. In one embodiment, the system may provide an indication (e.g., at block 204) of a similar patient to a user. This may be accomplished through a user interface, and may be performed automatically by the system upon the receipt of one or more signals. For instance, the system may provide the indication upon receipt of new patient information, a change in grouping information, an update of information, or any other triggering activity.

In one optional embodiment, the system may provide a control (e.g., as in block 205) that allows the physician or other practitioner to contact another physician that is associate with the patient identified to be similar to the current patient. As discussed, the control may permit communication between physicians, but in one implementation, such communication may be anonymous without the need to identify a specific patient and/or physician. At block 206, process 200 ends.

Figure 3:
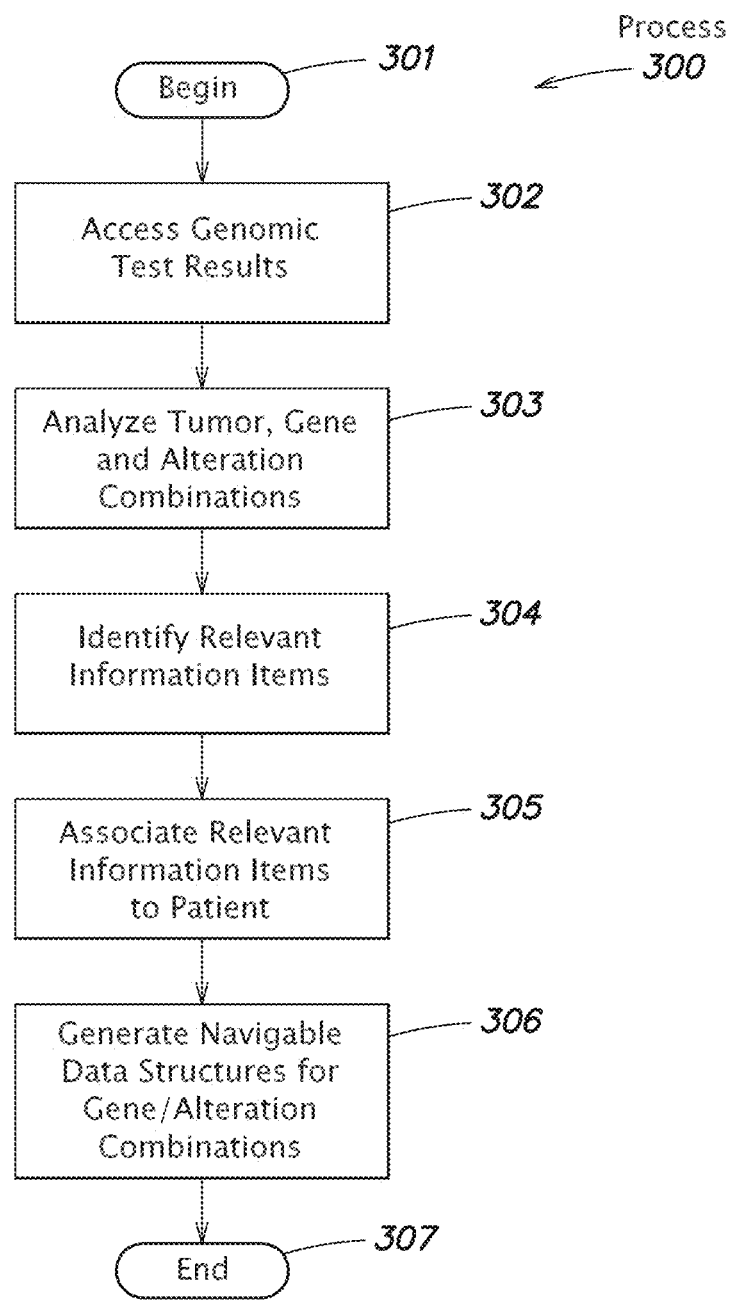
FIG. 3 shows an example process for creating a genomic database that may be used with various aspects of the present invention.

FIG. 3 shows an example process 300 for creating a genomic database that may be used with various aspects of the present invention. Shown in FIG. 3 is an example process flow 300 for managing genomic testing information. The process 300 begins at block 302 with access to genomic test results. According to one embodiment, genomic test results include information specific to a patient's tumor type, one or more genes implicated by the tumor, and alteration type associated with the one or more gene. At block 303, the tumor type, gene, and alteration combinations for the patient's cancer are analyzed, and relevant information items are identified at 304.

In some embodiments, the relevant data items can include clinical trials that match on any one or more of tumor type, gene, and alteration. The relevant data items can also include therapies or references that match on tumor, gene, and/or alteration. In some example, the relevant data items are stored for analysis at block 304 based on activity of curators. In one example, human curators can review clinical trial information (e.g., criteria, gene/alteration target, trial therapy, trial drug) and associate that clinical trial information with tumor types, genes, and/or alterations. The human curators can also review and characterize information on therapies and reference for use in, for example, process 300.

Once relevant information is identified, for example, at block 304, any relevant information item can be associated with the patient having the matching tumor type, gene, and/or alteration at 305. The association(s) defined at block 305 can be used at block 306 to generate navigable data structures which can be configured to organize gene and alteration combinations and links to any associated relevant information (e.g., identified at block 304 and associated at 305). In some embodiments, the navigable data structures can be presented within a user interface display.

In other embodiments, the relevant information identified at block 304 can be associated with patient records and/or specific genomic tests at block 305 based on a specified data model. Further, association of the relevant information at block 305 can include generation and storage of the associated information a data unit (e.g., information item) and the data unit can then be associated with the patient, and/or a gene or alteration in the patients genomic test results through a navigation link. The navigation link can be used as part of a dynamic display for a specific gene/alteration combination. Responsive to selection of the link, the dynamic display can transition to the relevant information.

Figure 4:
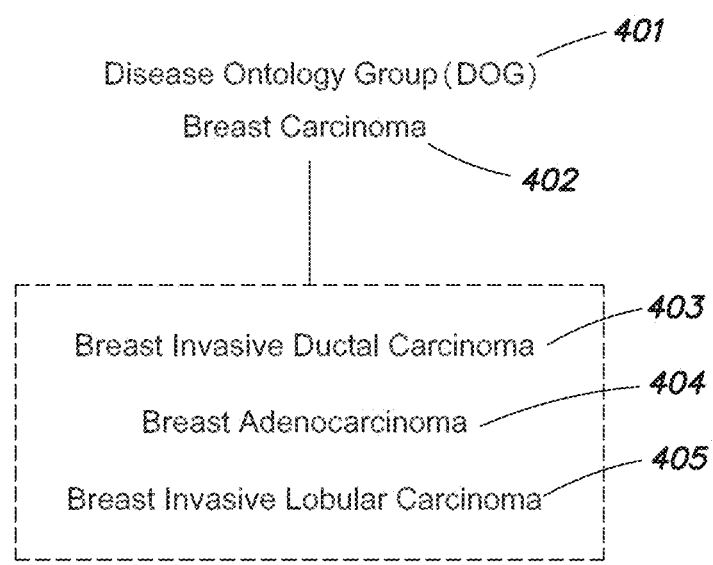
FIG. 4 shows disease ontology grouping that may be performed according to one embodiment of the present invention.

FIG. 4 shows disease ontology grouping that may be performed according to one embodiment of the present invention. For instance, a disease ontology group 401 may be made and stored as part of a database. More particularly, patient data may be grouped and accessed by disease ontology groups that link similar diseases. For instance, behavior and/or other characteristics of particular diseases may allow them to be grouped together. For instance, certain diseases may share common information such as alterations, progression of disease state, common treatments, clinical behavior or other information that would allow them to be grouped together. For instance, a more general DOG may be determined called "Breast Carcinoma" 402 which is a grouping of similar carcinomas including breast invasive ductal carcinoma 403, breast adenocarcinoma 404, and breast invasive lobular carcinoma 405. Such grouping may be used as a way of grouping related patients. For instance, patient data may include one or more disease types represented in a database by a relation to those disease types. Upon performing a query based on a particular defined DOG, patients having diseases categorized within the DOG may be obtained.

Figure 5:
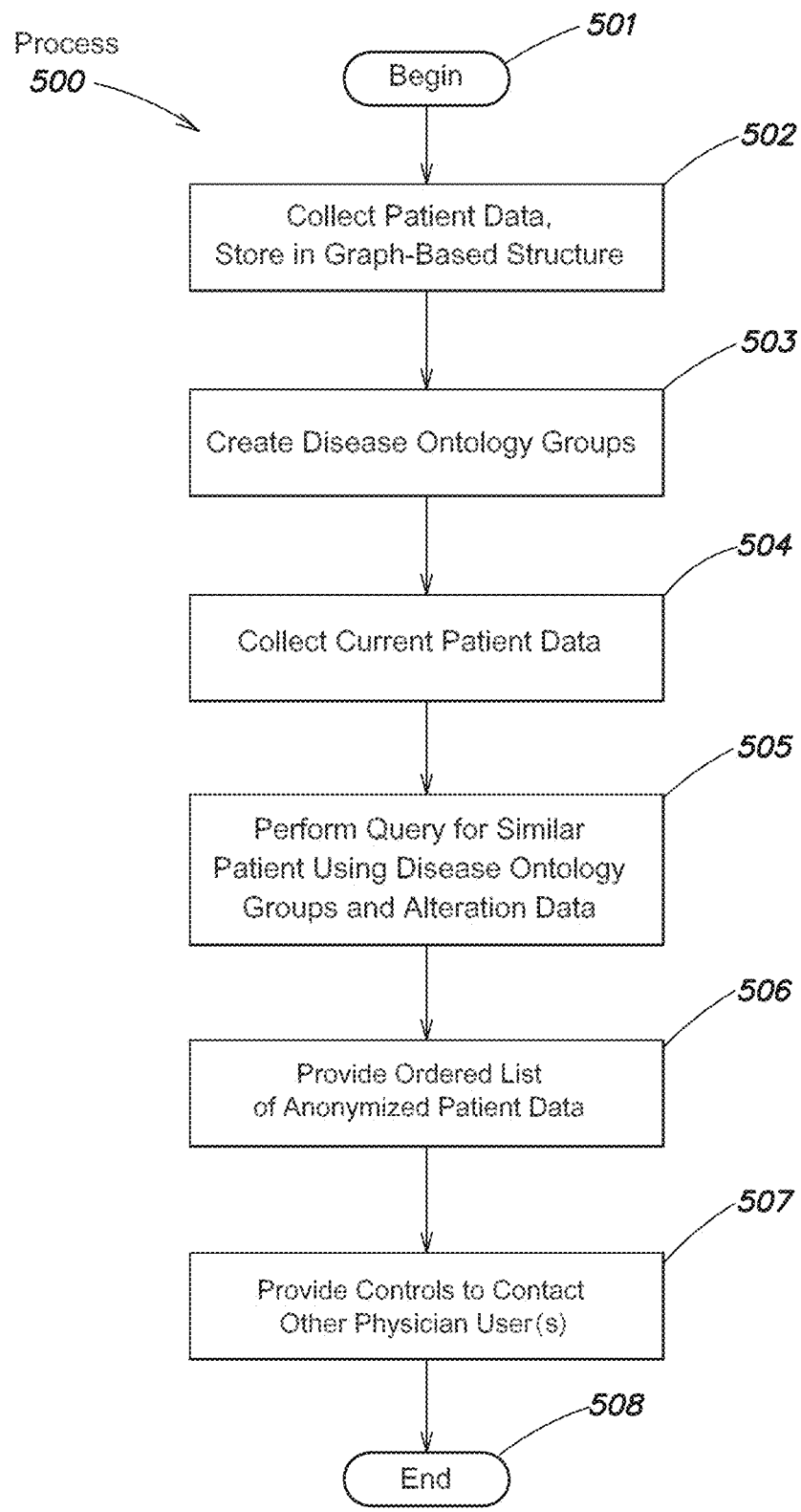
FIG. 5 shows an example process that may be performed locating similar patients using disease ontology groups according to one embodiment of the present invention.

FIG. 5 shows an example process 500 that may be performed locating similar patients using disease ontology groups according to one embodiment of the present invention. At block 501, process 500 begins. At block 502, the system (e.g., system 100) collects patient data and stores the patient data in a data structure in memory. As discussed, the data may include patient identification information, the patient's tumor/disease type, detected alterations for particular genes, treatment information, among other patient-related information. According to one embodiment, the information may be stored in a graph-based data structure. For instance, information may be stored in a database as discussed in more detail in U.S. patent application Ser. No. 14/463,068 entitled "SYSTEM AND METHOD FOR MANAGING GENOMIC INFORMATION" filed Aug. 19, 2014, which forms an integral part of this application. It should be appreciated that other databases may be used. However, it should also be appreciated that such a database may be used for collecting data from a number of sources, and may be preferable in cases where sparse data sets are used.

At block 503, disease ontology groups may be formed. For instance, as information is collected from various patients, studies, articles, etc., some diseases may have characteristics that may permit them to be grouped such as common treatments, similar alterations, etc. Such groupings may be performed automatically through collection of information from a number of sources and/or curated by experts who have specific knowledge of their relatedness.

At block 504, the system collects information regarding a current patient. For instance, a patient's tumor may be analyzed to determine alterations present. Such information may be stored in the database. In one embodiment, information may be stored in the form of tuple information including two elements connected by a relation (e.g., patient A has a diagnosis of metastatic melanoma, patient A has an alteration of BRAF 600E, etc.).

At block 505, the system may perform a query for a similar patient to the current patient entered using disease ontology groups and alteration data. For example, as discussed, data may be sparse, and groupings of similar alterations and diseases may permit a query to obtain results even if the disease/alteration combination of the current client is not found. However, as more patients are treated and their information stored, the system becomes more useful as a tool for locating client having similar disease structure. The query may be a two or more dimensional query that searches for similar patients belonging to a common alteration group and having a common disease ontology group as the current patient. A result may include an ordered list of patients.

At block 506, the system may provide the ordered list of patients to the physician user (e.g., within an interface of a computer system). In one embodiment, the patient data may be anonymized such that personally-identifiable information is masked or omitted from the physician computer interface. The list may be ranked such that the most relevant information is provided. Further, information for patients having positive outcomes may be preferred over negative outcome data, such that physicians are connected with other physicians that have successfully treated similar cancers. Further, information regarding a treating physician may also be used to order results, as in one example, a physician that has successfully treated a number of patients may be preferred over a physician that has only treated one similar patient. However, it should be appreciated that outcome data may not be included with respect to identifying similar patients, as some outcome data may be biased.

At block 507, the system may provide controls that permit the physician user to contact other physician user(s) that treated the identified patients. For instance, tools that captively collect the communications between physicians may be provided such that information is collected and saved in the database for use with future patients. In one embodiment, once it is identified that the database includes patients that are similar to a current patient, the physician user caring for the current patient may be contacted. Further aspects of the present invention relate to selecting the patient for which a physician may be contacted.

The system may also include a number of timer and reminder functions to facilitate the communications such that the requesting physician is provided the information in a timely manner to support treatment of the patient. At block 508, process 500 ends, although it is appreciated that this process may be repeated many times, constantly improving the database with new data including treatments, communications and patient outcomes.

Figure 6:
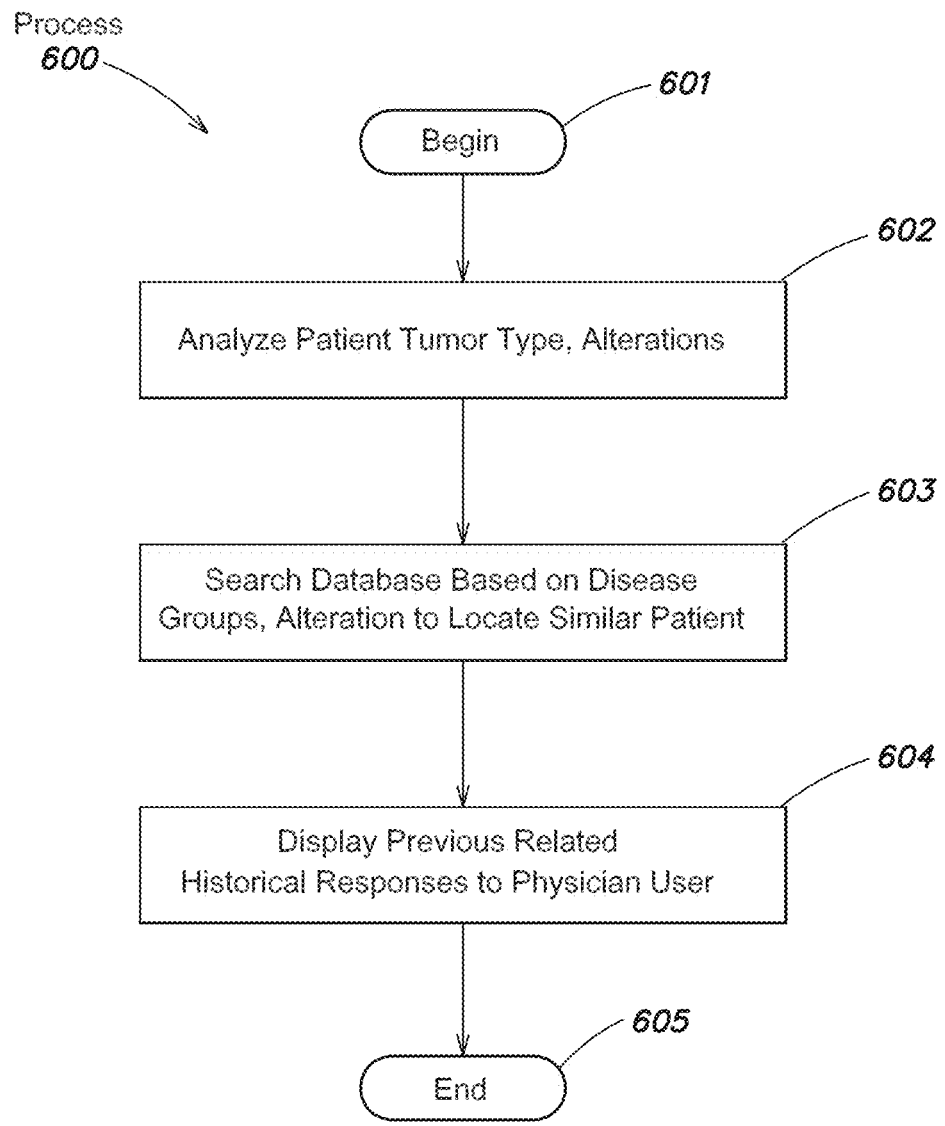
FIG. 6 shows an example process for locating historical responses and presenting them to physician users according to one embodiment of the present invention.

FIG. 6 shows an example process 600 for locating historical responses and presenting them to physician users according to one embodiment of the present invention. At block 601, process 600 begins. At block 602, a patient's cancer may be analyzed through one or more processes, including genomic testing. It is appreciated that through genomic testing of a patient's cancer, a targeted treatment for the particular cancer can be created, which is more effective and less damaging of other types of cells.

At block 603, the diagnosed tumor type and related disease group and present alterations and related alteration group is used to locate one or more similar patients. For example, if specific patients identified have an identical disease and alterations, patients are identified and returned as a result. However, if no exact matches are found, patients belonging to the same alteration disease groups may be returned. In another embodiment, a more general search using the identified groups may be performed rather than a two-step approach.

At block 604, the system may be adapted to display any previously related historical responses to the physician user. For instance, depending on whether a previous search was performed using similar disease and alteration combinations, there may exist existing response data within the database between physicians. It may be beneficial to store such information and provided to physicians without the necessity for contacting the treating physician again for the same information. At block 605, process 600 ends.

Figure 7A:
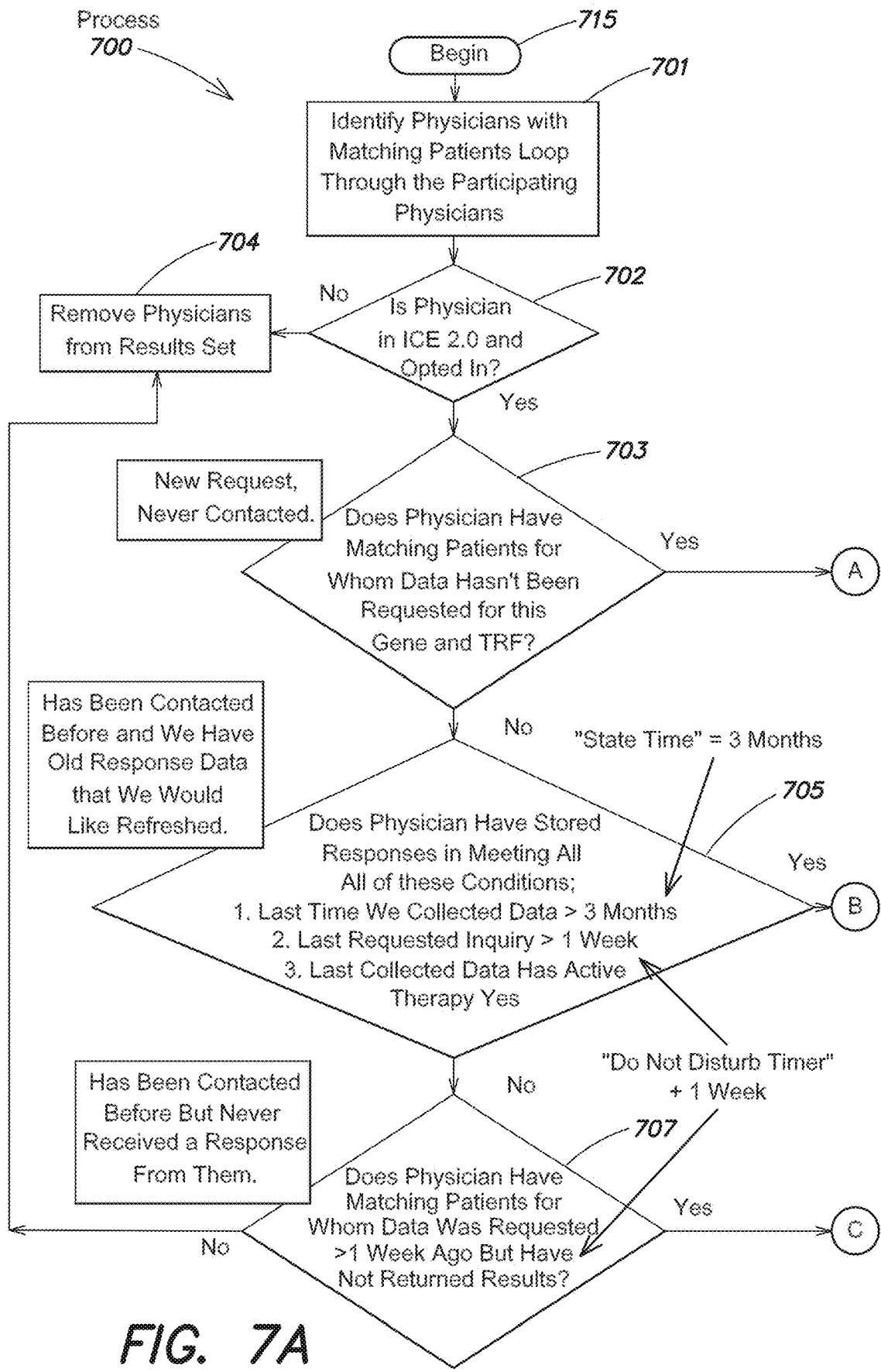
FIGS. 7A-7C show an example process for conducting a communication session between physicians according to one embodiment of the present invention.
Figure 7B:
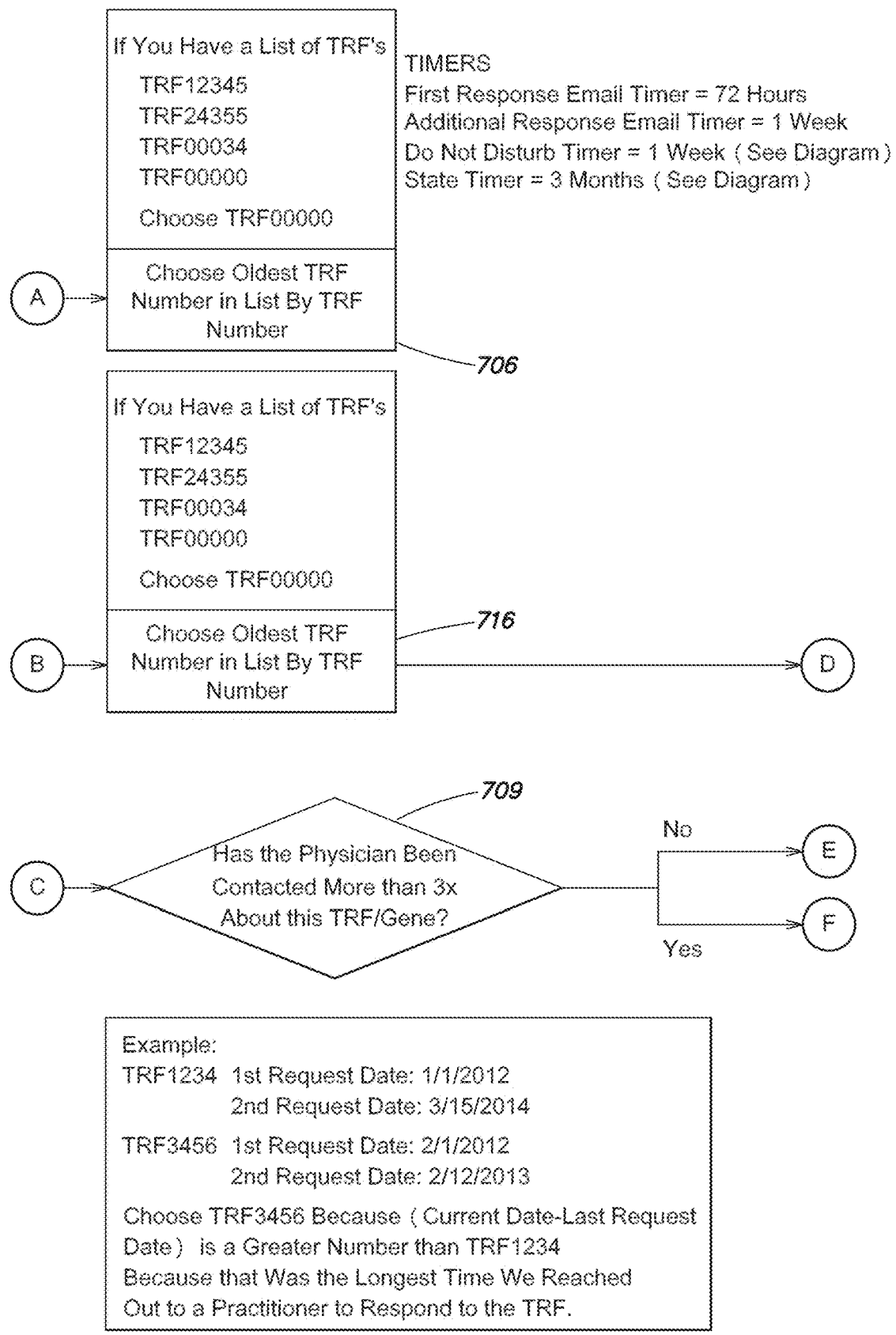
Figure 7C:
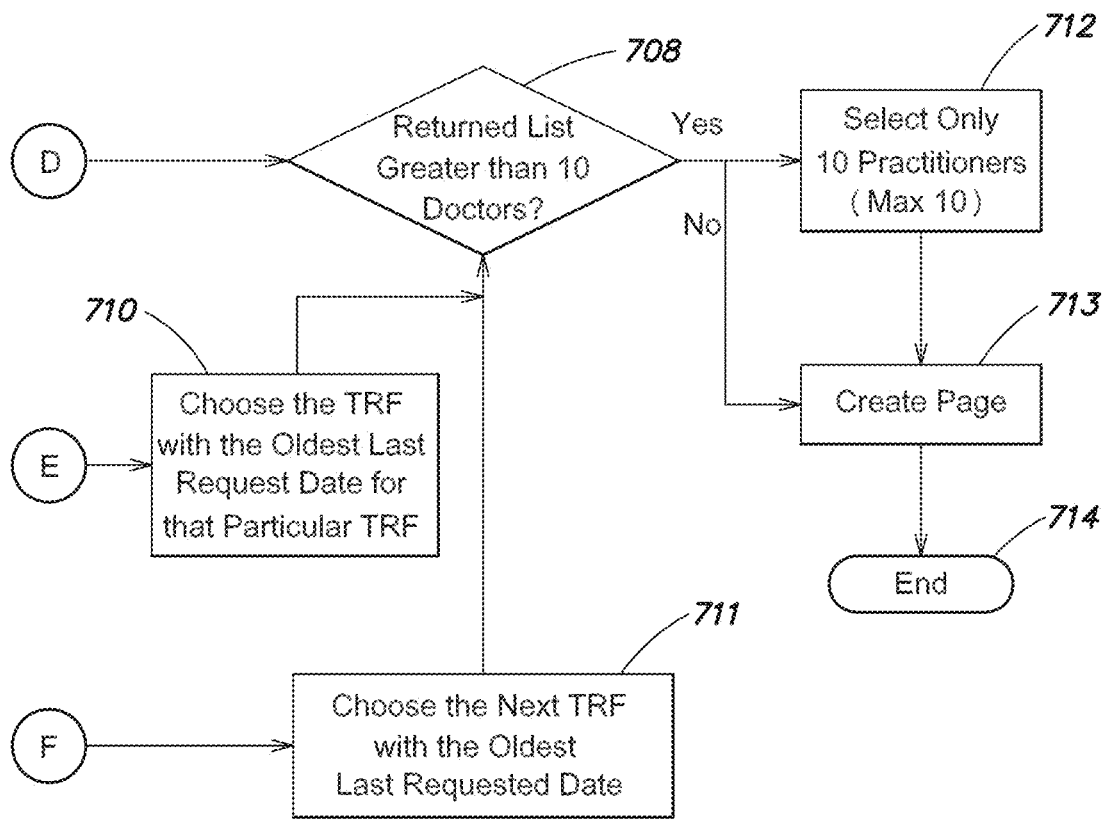

FIGS. 7A-7C show an example process 700 for conducting a communication session between physicians according to one embodiment of the present invention. At block 715, process 700 begins. At block 701, the system identifies physicians having matching patients, and begins a looping process through the list of participating physicians. For example, in one embodiment, physicians may opt in to participate in providing additional information and communicating with other physicians about their patients. At block 702, it is determined whether a physician within the system (referred to herein as the Interactive Cancer Explorer (ICE) system) has opted in to receive communications from other physicians. If not, the physician may be removed from the result set at block 704.

However, if the physician has opted in, it is determined at block 703 whether the physician has matching patients for whom the data has not been requested for this particular gene and individual record numbers uniquely identifying a report relating to a particular patient. Such an individual record number is referred to hereinafter with respect to FIGS. 7A-7C as a TRF number. If the physician has matching patients, block 706, the system chooses the oldest TRF number in the list. If at block 708, it is determined that the returned list includes greater than 10 practitioners (or other predetermined number of practitioners), then only 10 practitioners (or the specified predetermined amount) are returned at block 712. If there are less than 10 practitioners identified, then a result page is created and displayed including the identified doctors. Alternatively, if more than 10 doctors are identified, then only 10 doctors are identified in the created page.

If, at block 705, it is determined the physician has stored responses saved within the system that meet the specified criteria, then information is selected for particular cases to be displayed to the user. For instance, at block 716, the system may choose the oldest TRF number in the list and display that particular case to the physician user. Such criteria may include, for instance, a collection of data that relates to how stale information is within the database, how active the cases by collected data or when the data was last requested.

If, at block 705 it is determined that there is no data for particular physician, is determined at block 707 whether the physician includes matching patients for whom data was requested greater than a predetermined time but yet has not returned any results. If not, the physician may be removed from the result set at block 704. However, if the physician has not yet been contacted more than a predetermined number of times (e.g., three times) regarding this TRF, the next TRF may be chosen at block 711 with the oldest last requested date. If the physician has not been contacted more than the predetermined number of times, the TRF with the oldest last requested date for the particular TRF may be chosen at block 710. As a result of identifying the most current information, responsive physicians, and relevant patient information, a page output may be constructed and displayed to the physician user at block 713. At block 714, process 700 ends.

Figure 8:
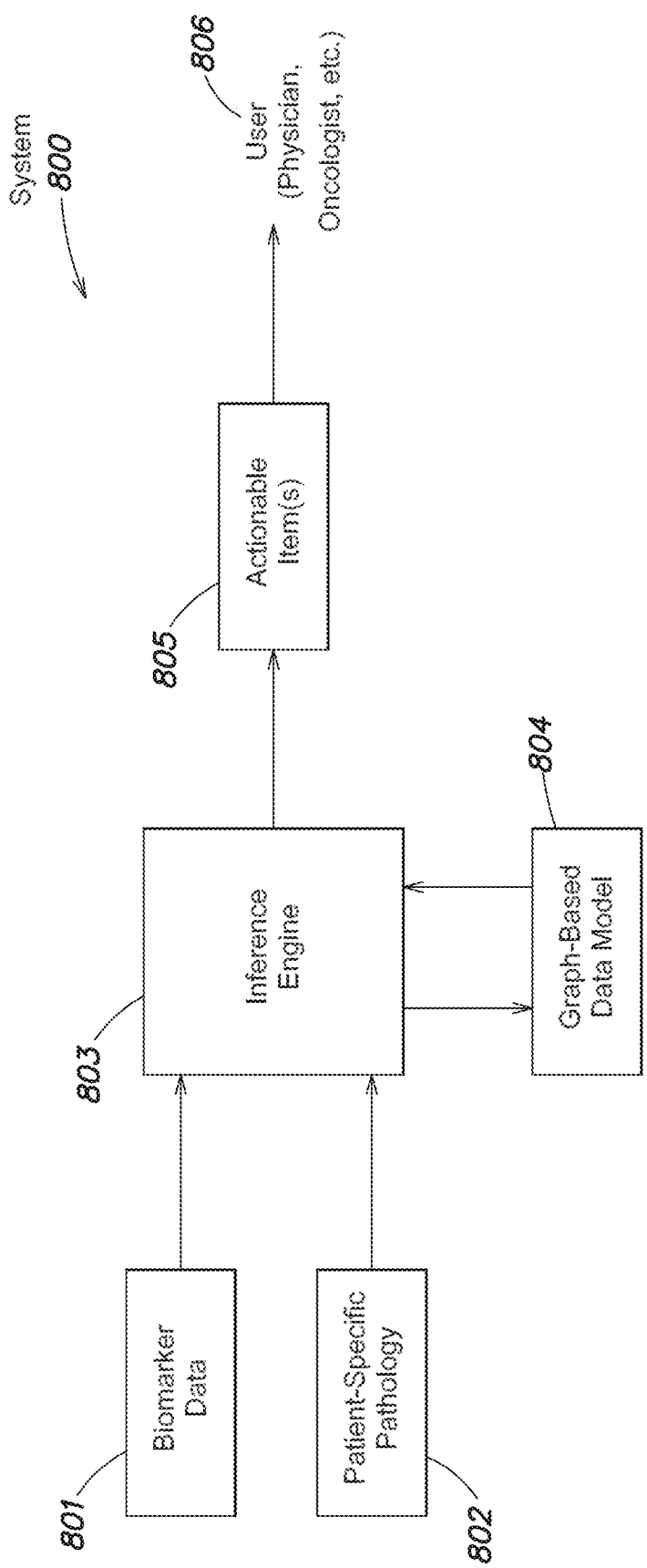
FIG. 8 shows an example system upon which various aspects of the present invention may be practiced.

FIG. 8 shows an example system upon which various aspects of the present invention may be practiced. FIG. 8 shows a system 800 which may include one or more computer-based systems that receive and collect biomarker data 801 and patient specific pathology information 802. System 800 includes an inference engine 803 that interprets a graph-based data model 804 to determine one or more actionable items 805. Such actionable items may be presented to a user 806 (e.g. a physician, oncologists, or other user type). Such actionable items may include recommending a patient for clinical trial, a recommendation of a particular form of treatment, or other recommendation.

Such a model may be a learning model in that information is being added to the system in real time, and the recommendations made by the system may also change over time. For instance, information may be added, deprecated, deleted, or updated, such as adding information relating to patients, studies, journal articles or other information. Additional information may be added as tuples to the graph-based data model. The inference engine may use such additional information to make one or more inferences regarding the data model.

Example Genomic System

Figure 9:
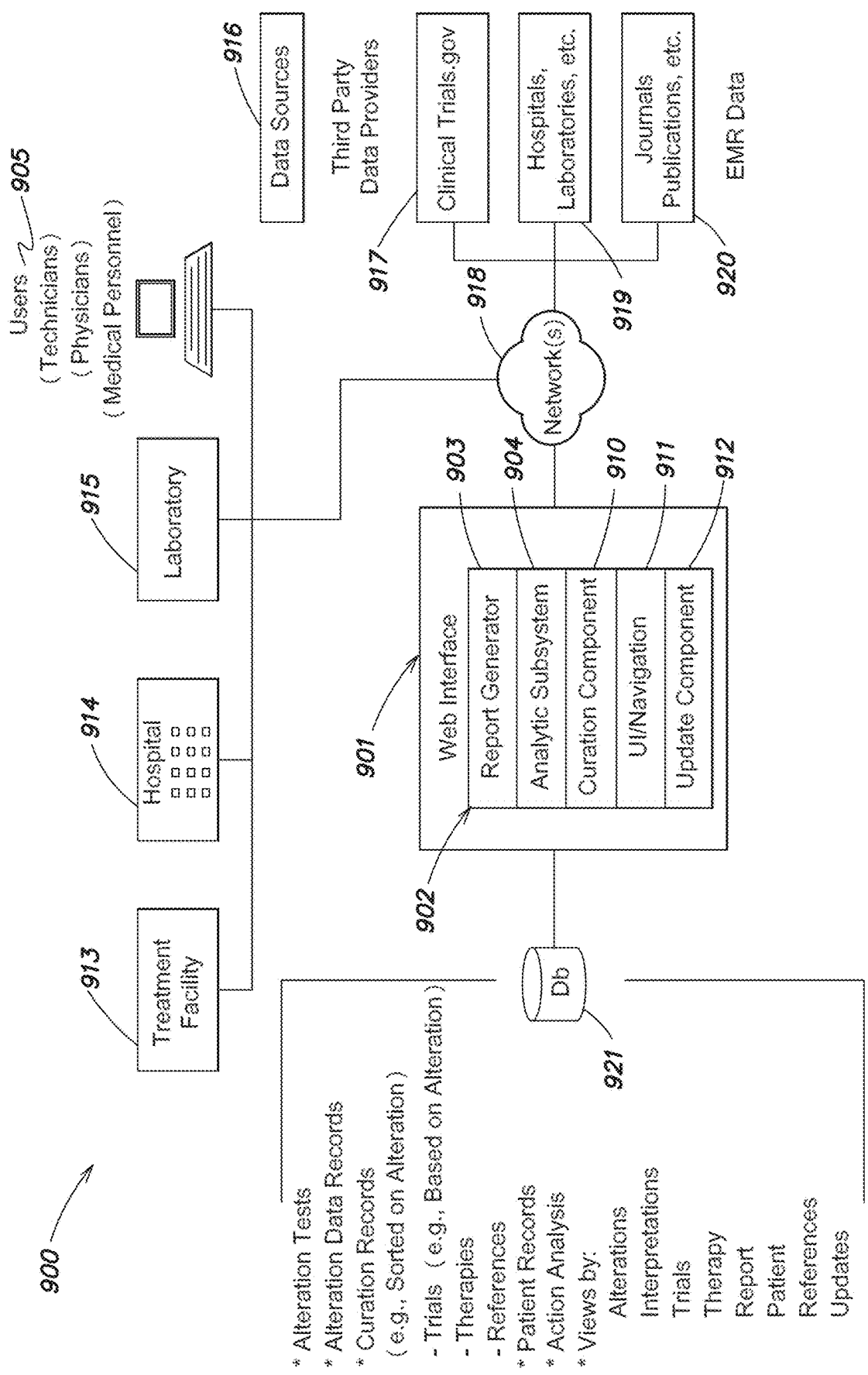
FIG. 9 shows yet another example system upon which various aspects of the present invention may be practiced.

FIG. 9 shows yet another example system upon which various aspects of the present invention may be practiced. In particular, FIG. 9 shows an example embodiment of a system 900 for managing genomic testing information. The system 900 can be configured to provide a single reporting source for accessing and applying available information on a patient's cancer. According to some embodiments, genomic testing on the patient's cancer provides specific information the tumor, one or more genes implicated by the tumor, and one or more alterations within the genes which can be displayed by the system 900 through a web interface 901. In some embodiments, the web interface 901 can include an alteration engine (e.g., element 902) that performs any of the operations discussed below with respect to the alteration engine 1001. For example, the web interface and/or alteration engine can be configured to use the testing information on tumor, gene, and alteration for a patient to manage delivery of curated information to end users (e.g., technicians, physicians, medical personal, etc.) over a communication network (e.g., 918). In one embodiment, the alteration engine can include a UI or navigation component 911 configured to generate displays that focus users (e.g., physicians) on actionable information within the genomic test results and associated information. For example, the UI component 911 can display navigable data structures including information on genes and alterations identified in a genomic test coupled with indicators informing the user of available actionable information associated with a patient's cancer.

According to some embodiments, the alteration engine can include specific component for provide specific functionality on the web interface 901. For example, the alteration engine 902 also can include a report generator component 903 configured to generate physical and/or static report for downloading through the web interface. The alteration engine can also include an analytic subsystem 904 an analytic subsystem configured to identify matches information between a current patient's tumor type, gene, and/or alteration and include or identify the matching information items for display in the patient's test results.

According another embodiment, the alteration engine 902 can also include a curation component 910 configured to generated curated information for use on the system. The curated information can include interpreted statements regarding any one or more of genomic alterations, an implicated gene, a patient's tumor type, and/or potentially applicable therapies for a patient's cancer. In some examples, the curation component can be accessed by human operators "curators" who generate and/or approve system generated interpreted statement regarding genomic alterations, an implicated gene, a patient's tumor type, and/or potentially applicable therapies.

As discussed, the alteration engine can also include the UI component 911 configured to generate and display navigable data structures which include information on genes and alterations identified in a genomic test, which can be coupled with indicators for actionable information associated with a patient's cancer. The UI component 911 can transition the system to the actionable information (e.g., therapy information items, trial information items, reference information items) responsive to selection in the user interface. Further, the UI component may be modified to allow physicians to communicate information responsive to identifying similar patients.

In further embodiments, the alteration engine can include an update component 912 configured to track any updates to genomic alterations and any information associated with the genomic alterations. In one embodiment, the update component 912 can identify updates information for display by the UI component 911. Various embodiments, of the alteration engine components are configured to perform the function and operations discussed above with respect to the alteration engine and associated components.

According to some embodiments, the web interface 901 can be accessed by users (e.g., 905) over the internet. The user can access the web interface from a variety of location (e.g., laboratory 915, hospital 914, and treatment facility 913). In various embodiments, the users at any one or more of 913-915 can share genomic test reports with each other. For example, the web interface 901 can be configured to provide social functions between users. In some embodiments, the web interface can limit sharing to practice groups, within treatment facilities, or within medical institutions (e.g., hospitals). According to one aspect, sharing of test results and associated genomic information on patients can create a strong community of physicians, and foster discussion about treatment. Further, as discussed above, the interface may permit identification of similar patients and foster collaboration about similar patients.

According to some embodiments, the web interface 901 is adapted to store genomic test information in database 921. Database 921 is illustrated as a single database, but in other embodiments, database 921 can include any storage medium or organizational unit for storing and accessing genomic test results and associated information. Further embodiments can include a plurality of databases and can also include distributed data architectures. According to one embodiment, database 921 can include a variety of data records accessed by the web interface 901 to manage delivery of genomic test results and associated information.

For example, the database can include information on genomic testing. In one example, genomic test results are stored and associated with patient records. The genomic test results can include information on genomic alterations. Specific genomic alterations can be stored in database 217 and access for presenting information within a display of a patient's test report. The database can include curation records stored and associated with any one or more of a tumor type, gene, and/or genomic alteration. Other information may be stored, such as disease ontology groups, alteration groups, communications between physicians, outcome information, and/or any other type of information. Information on clinical trials can likewise be stored as information items associated with any one or more of a tumor type, gene, and/or genomic alteration. The database 921 can also store therapy information and references information and provide associated for either to any one or more of a tumor type, gene, and/or genomic alteration. The database 921 can also be configured to track and store information on updates to any information within the database. In one example, updates can be flagged by other system components and the flags resolved or remove once viewed.

In further embodiments, the database can store information on data views for used by web interface and/or the UI component 911. Each one of the views can be accessed and used by the web interface to present information on genomic testing and associated information to a user. In some examples, the system and/or web interface can be configured to capture information from external information sources for storage in database 921. In one example, external data source 916 can contain information related to a patient's tumor type, gene, and/or alteration. The information from the external information can be captured and stored as records in database 921 accessible via the relationship to the tumor type, gene, and/or alteration.

According to some embodiments, the information stored in database 921 can include reference to the external information source. For example, clinical trial information items can include links to clinicaltrials.gov 917, reference information items can include links to PubMed.gov (e.g., 228). In further embodiments, the web interface 202 can be configured to access genomic alteration information for cancer diagnoses made at a hospital or laboratory (e.g., 919). For example, the web interface can capture genomic information from EMR (electronic medical records) data to retrieve tumor type, implicated gene, and/or alteration type for storage in database 921. In some implementations, references or links to the specific medical records can also be stored in the database. In one example, the links to the medical records can be presented in a dynamic display generated on system 900.

According to one aspect, the database 921 and all associated information can be organized or accessed based on one or more of tumor type, gene, and alteration. In one embodiment, the tumor type, gene, and alteration data is stored as a data unit (e.g., a tuple). The data unit can be used by the system to identify or display related information based on matching any one or more of the tumor type, gene, and alteration. In further embodiments, each data unit can be linked to actionable information (where it exists). For example, each data unit can be linked to a matching therapy (e.g., a therapy information item describing a specific therapy, application, etc.). In another example, data units can be linked to a matching clinical trial (e.g., stored as a clinical trial information item).

According to one embodiment, associated of all the information in the database according to tumor, gene, or alteration provides insight into prescribed uses of therapies (on-label) and off-label applications for such therapies. In one example, off-label used can be identified based on alteration (e.g., different tumors but same alteration—provides relation information on a potentially effective therapy the current patient's cancer.

According to another embodiment, each record can be associated with a data space for an update flag. Responsive to any update to information on the database 921, the system can enter information in the data space for the update flag. Tracking updates to genomic alteration and associated information facilitates user awareness of potential significant changes in a patient report. Further, tracking of update information in the database 921 enables the system to deliver notification regarding any updates.

In some further embodiment, social functions can have associated records in the database. For example, permission information (e.g., who can share a report and/or who can receive a shared report) can be associated with test reports stored in database 921. Further, communication sessions between physicians may be stored as records within the database.

Figure 10:
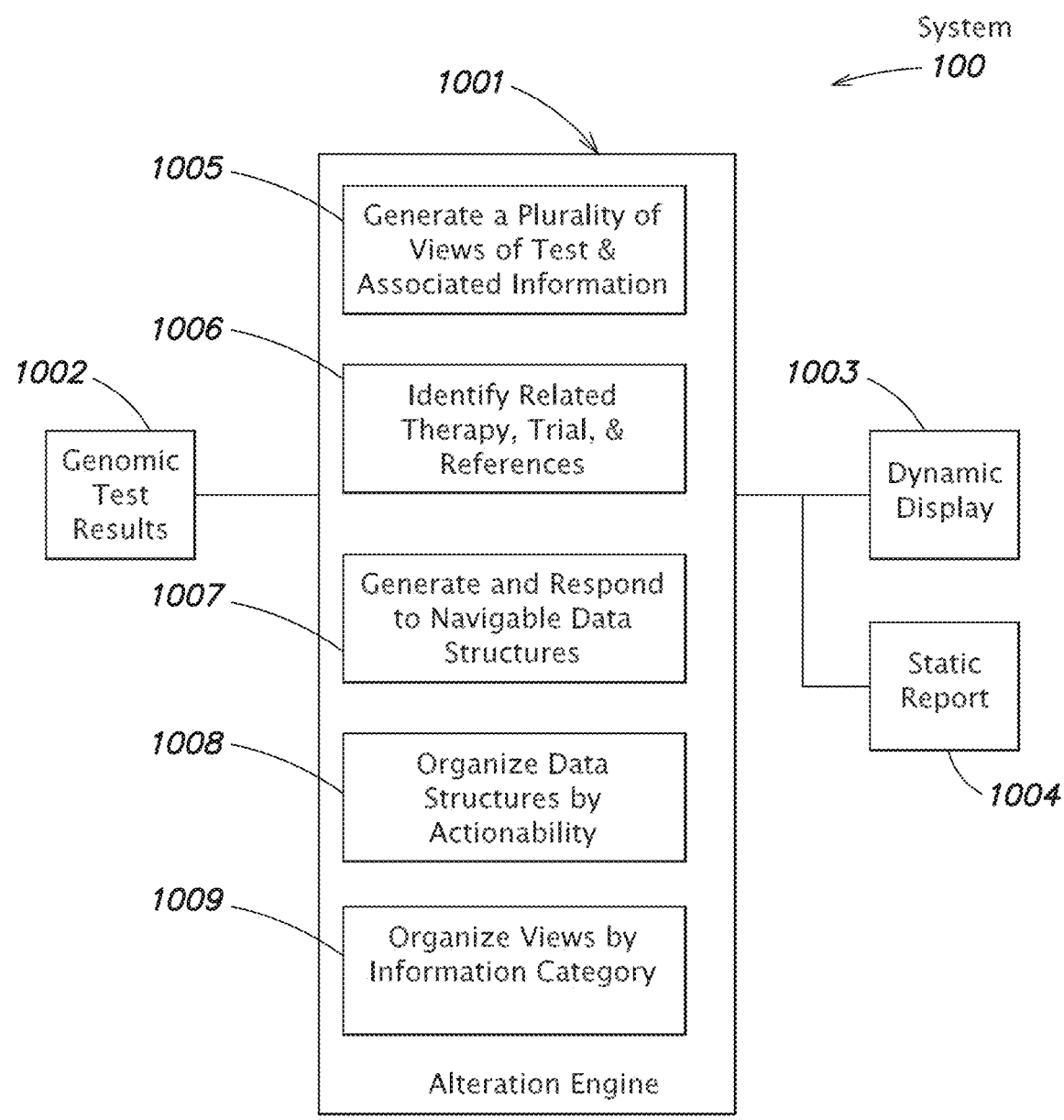
FIG. 10 shows another system there may be used to generate data from genomic test results according to various aspects of the present invention.

FIG. 10 shows another system that may be used to generate data from genomic test results according to various aspects of the present invention. As described above, genomic testing provides unique opportunities to make more informed treatment decisions, especially in the field of cancer diagnosis and therapy development. Some conventional approaches can fail to provide useable information within the volumes of information provided as results of genomic testing. Further, it is appreciated that some conventional approaches fail to focus practitioners on actionable information within the genomic testing information and any associated treatment information.

Accordingly, provided are systems and methods for managing genomic testing information that provide a single reporting source for accessing and applying available information on a patient's cancer. According to some embodiments, genomic testing on the patient's cancer provides specific information on the tumor, one or more genes implicated by the tumor, and one or more alterations within the genes. The testing information on tumor, gene, and alteration can be used by the system to manage delivery of curated information that focuses users (e.g., physicians) on actionable information within the genomic test results and associated information. For example, publically available data (e.g., therapy data, clinical trial data, and journal publications) can be interpreted to provide the curated information based on its relationship to one or more of the tumor, gene, and alteration for a patient. The publically available information can be processed on the system to provide navigable data structures informing the user of available actionable information associated with a patient's cancer.

According to one embodiment, by providing users an indicator of actionable information, information within genomic testing reports can be provided succinctly and enable the users to select the indicator to access more detailed information as needed. Further, genomic test results (e.g., listings of alterations) can be ordered based on the presence or absence of actionable information items. In one example, actionability of the navigable data structures can be defined on available information for an FDA approved agent in the patient's tumor type, available information for an FDA approved agent in another tumor type, and/or available information for a mechanistically driven or biologically relevant clinical trial based on the alteration(s) found.

The ordering can be configured to focus the user on the actionable information to facilitate review of a plurality of alterations and their associated information. Indicators of actionable items can be displayed based on an information source (e.g., a therapy indicator/tag references available therapy information items related to a genomic alteration, a trial tag references available clinical trial information items, and a reference tag for reference information items). The indicator can be associated with a respective alteration in the plurality of alterations resulting from genomic testing.

In some embodiments, the system facilitates successive selection of alterations and associated information within the plurality of alteration results, for example, using the indicators. By enabling successive selections, the system facilitates better understanding of a patient's cancer and enables more informed treatment decisions.

According to some embodiments, the actionable information includes identification of FDA approved therapies for a tumor, gene, and alteration combination. Actionable information can also include identification of related therapies that are implicated by any one or more of the tumor, gene, and alteration characteristic of a patient's cancer. According to some embodiments, related therapies can be determined by the system and displayed to users to facilitate treatment decisions. For example, indicators regarding the related therapies can be displayed as part of the navigable data structures within user interface displays generated by the system.

Referring to FIG. 10, there is illustrated an example of a system 1000 for managing genomic testing information using an alteration engine 1001. Elements of the system 1000 can be provided using a computing system such as a computer system such as that described above with reference to FIG. 9. For example, the alteration engine 1001 can be executed on the computer system to provide the functions and operations discussed herein. In other embodiments, the alteration engine 1001 can include additional components executed on the computer system to perform specific operations.

As shown in FIG. 10, various embodiments of the alteration engine 1001 are configured to accept genomic test results 1002 and associate the genomic test results with curated information. The curated informing can include detailed analysis or additional information tailored to the characteristic of the test results. For example, the test results generated for a specific patient can specify a plurality of genes and alterations found within the patient's cancer. The alteration engine 1001 can be configured to associate curated information tailored to the specific genes/alteration identified for the patient.

In some embodiments, the alteration engine 1001 can be configured to generate a single source display of the test results, curated information, and any additional information (e.g., identified similar patient data) as a dynamic display 1003. The dynamic display 1003 can include and organize the test results, the curated information, and the additional information to minimize the volume of data displayed to the user at any one time. According to one embodiment, the dynamic display 1003 can include a plurality of views of the test results, the curated information, and the additional information. In one example, the test, curated, and additional information can be organized into categories for display in a user interface. In some embodiments, the user interface can be specially configured for navigation with mobile devices.

The user interfaces generated by the system can also be configured to include gene and alteration information specific to a current patient being viewed. The user interfaces are configured to present categorized information to facilitate understanding of the gene and alteration information for the current patient. In one example, the dynamic display is presented for a specific patient selected by the user from a patient listing. Once selected, the current patient's information (e.g., name, date of birth, height, weight, sex, patient id, case id, etc.) can be provided along with information regarding the genetic testing conducted (e.g., specimen receipt date, report generation date, diagnosis (type of tumor), collection date for specimen, collection method, specimen type, etc.) as a first portion of a dynamic display 1003. If anonymized (e.g., the patient is not the user's patient) some or all of this identifying information may be masked or removed.

A second portion of the dynamic display 1003 generated by the system and/or alteration engine 1001 can include the results of the genetic testing organized by gene and alteration. In some embodiments, the alteration engine 1001 can include a user interface ("UI") component configured to generate and to provide for navigation within the dynamic display 1003. For example, each gene and alteration result generated from genomic testing of the current patient's cancer can be displayed as its own data structure. The data structure can contain selectable indicators of actionable information specific to each of the gene/alteration results. In one embodiment, the UI component is configured to transition the dynamic display 1003 to the actionable information in response to selection of the indicators.

In some embodiments, the alteration engine 1001 can be configured to generate a single source display of the test results, curated information, and any additional information (e.g., identified similar patient data) using a dynamic display 1003. The dynamic display 1003 can include and organize the test results, the curated information, and the additional information to minimize the volume of data displayed to the user at any one time. According to one embodiment, the dynamic display 1003 can include a plurality of views of the test results, the curated information, and the additional information. In on example, the test, curated and additional information can be organized into categories for display in a user interface. In some embodiments, the user interface can be specially configured for navigation with mobile devices.

The user interfaces generated by the system can also be configured to include gene and alteration information specific to a current patient being viewed. The user interfaces are configured to present categorized information to facilitate understanding of the gene and alteration information for the current patient. In one example, the user interfaces are presented for a specific patient selected by the user from a patient listing. Once selected, the current patient's information (e.g., name, date of birth, height, weight, sex, patient id, case id, etc.) can be provided along with information regarding the genetic testing conducted (e.g., specimen receipt date, report generation date, diagnosis (type of tumor), collection date for specimen, collection method, specimen type, etc.) as a first portion of a user interface. If anonymized (e.g., the patient is not the user's patient) some or all of this identifying information may be masked or removed.

A second portion of a user interface generated by the system and/or displayed by the dynamic display 1003 can include the results of the genetic testing organized by gene and alteration. In some embodiments, the alteration engine 1001 can include a user interface ("UI") component configured to generate and to provide for navigation within the user interfaces displayed by the dynamic display 1003. For example, each gene and alteration result generated from genomic testing of the current patient's cancer can be displayed as its own data structure. The data structure can contain selectable indicators of actionable information specific to each of the gene/alteration results. In one embodiment, the UI component is configured to transition the user interfaces displayed by the dynamic display 1003 to the actionable information in response to selection of the indicators.

Figure 11:
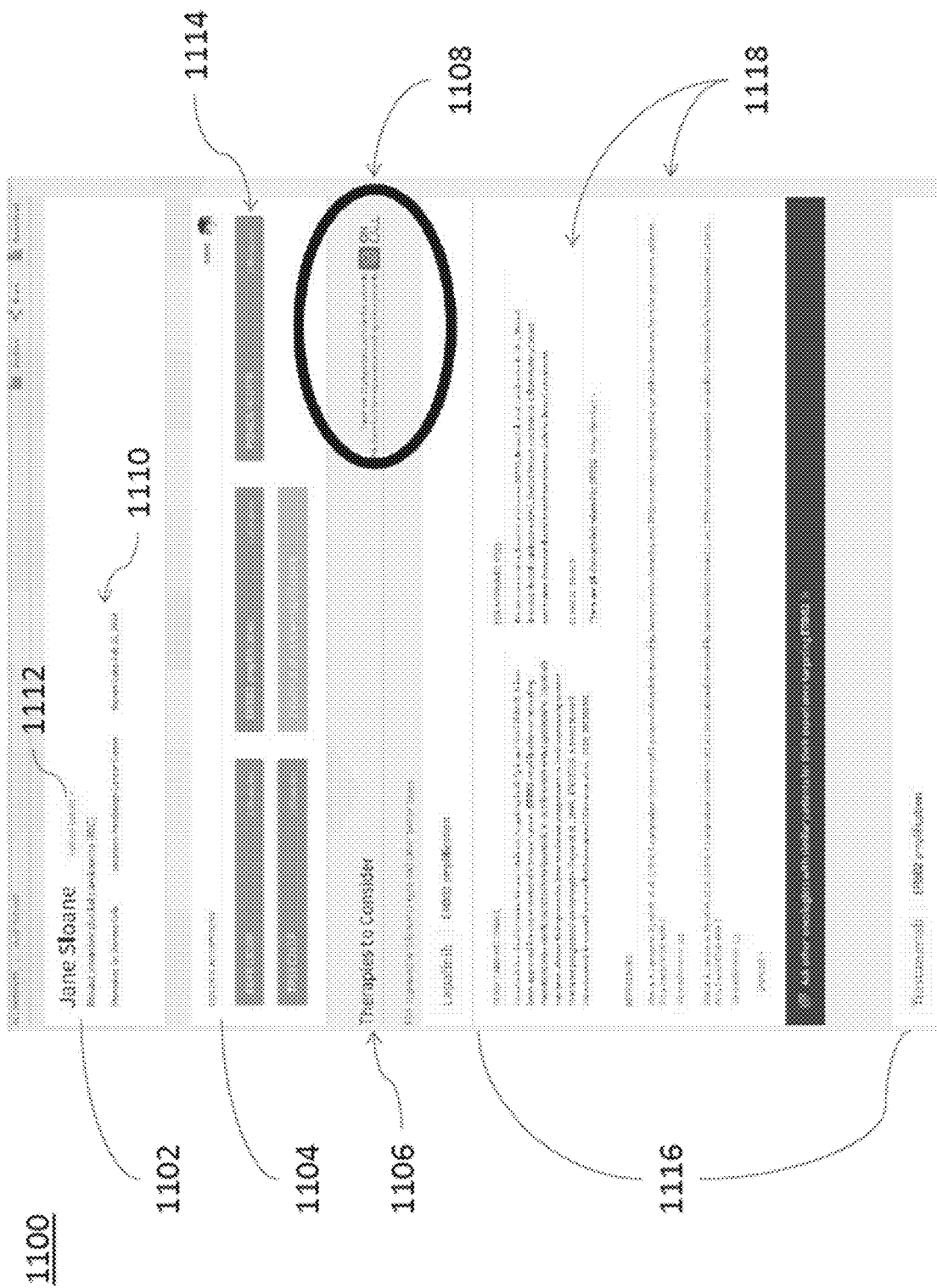
FIG. 11 illustrates one example of a user interface showing patient and treatment information according to one embodiment of the present invention.

For example, FIG. 11 illustrates a user interface 1100 that may be used to display patient information and potential therapies for one or more genomic alterations. In at least one embodiment, the user interface 1100 is configured to provide patient information 1102, genomic alteration information 1104, therapy information 1106, and/or an on call button 1108.

In certain embodiments, a patient list button 1109 is also provided. Responsive to selection of the patient list button 1109, a patient list user interface is displayed comprising a list of patients in the system. Selection of a patient from the list of patients is operable to display a patient information user interface similar to that of FIG. 11. In some embodiments, the user interface can include one or more filters (e.g., a diagnosis, a physician, a facility, etc.) to sort a list of patients.

The patient information 1102 includes general information 1110 about a patient, such as a patient name, a patient diagnosis, an attending physician, a diagnosis location, a date of report creation, and so forth. Furthermore, a patient details button 1112 is provided in some embodiments that can be expanded to display additional information about a patient, such as a patient's height, weight, date of birth, gender, and so forth.

According to some embodiments, a genomic alteration information 1104 section is provided to display genomic alteration information associated with a patient. For example, the genomic alteration information can include information identifying an abnormal gene associated with a patient, and how the abnormal gene has been altered (e.g., mutations, amplification, etc.). In one embodiment, the genomic alteration information 1104 section displays each genomic alteration 1114 in a list format and, responsive to selection of a specific genomic alteration, the system is operable to display therapy information 1106 pertaining to the selected genomic alteration.

In at least one embodiment, the therapy information 1106 section includes one or more selectable therapies 1116, displayed in a list format, that are associated with the selected genomic alteration. Selection of one of the one or more therapies 1116 provides expanded details 1118 about the selected therapy. For example, the expanded details 1118 can include target and rationale for the selected therapy, FDA-approved uses, clinical trial information, references pertaining to the selected therapy, and so forth.

In one embodiment, an on call button 1108 is provided, operable to connect a user with other users. For example, the other users can be physicians that have patients with genomic alterations similar or substantially identical to one or more of the listed genomic alterations 1114. In at least one example, selection of the on call button 1108 is operable to display a connection user interface illustrated by FIG. 12 below.

Figure 12:
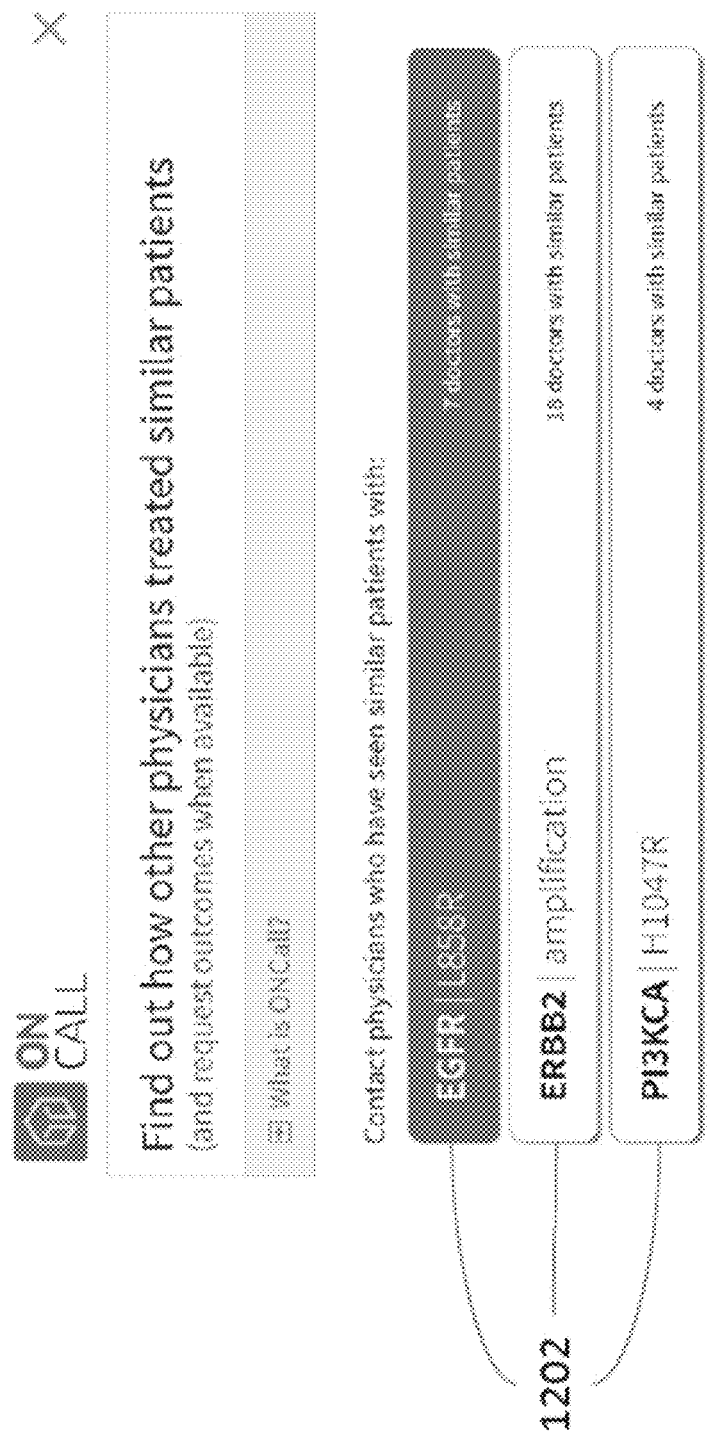
FIG. 12 illustrates another example of a user interface showing a connection user interface according to some embodiments of the present invention.

FIG. 12 illustrates one example of a user interface 1200 that is operable to connect a user with other physicians. For example, the user interface 1200 can include a list of each genomic alteration 1202 associated with a patient and, operable to selection of a genomic alteration 1202 from the list, navigate to a connection user interface configured to connect the user with physicians that have treated, or are treating, patients with the selected genomic alteration 1202. The system may include a matching engine that identifies similar patients within the database based on genomic alterations 1202, amongst other information. For example, in one embodiment, the connection user interface includes contact information for one or more other physicians and allows the user to send a message (e.g., an email message, a prerecorded voice message, etc.) to the other physicians. The message may be automatically generated by the system in some examples, while in other examples, the user may generate the message. In yet other embodiments, the system may pre-populate a message with a generic request, but allow the user to further modify or customize the message. Responsive to a user input, the message can be sent to any of the one or more physicians.

According to one embodiment, a user can receive a message indicating a request for information from one or more other users. For example, the user may have treated a patient with a specific genomic alteration, and a second user may request information about the treatment identified in the message. In some embodiments, the request is displayed by a user interface comprising a series of questions about the treatment for the specific genomic alteration. For example, the series of questions can include questions pertaining to a name of the treatment, a duration of the treatment, a patient response to the treatment, comments about the treatment, clinical trial notes about the treatment, and so forth. In at least one embodiment, a set of responses to the series of questions is accepted by the system in response to input from the user. The system compiles one or more responses to a request from one or more users and, in some examples, sends the compilation to the user that sent the request.

Figure 13:
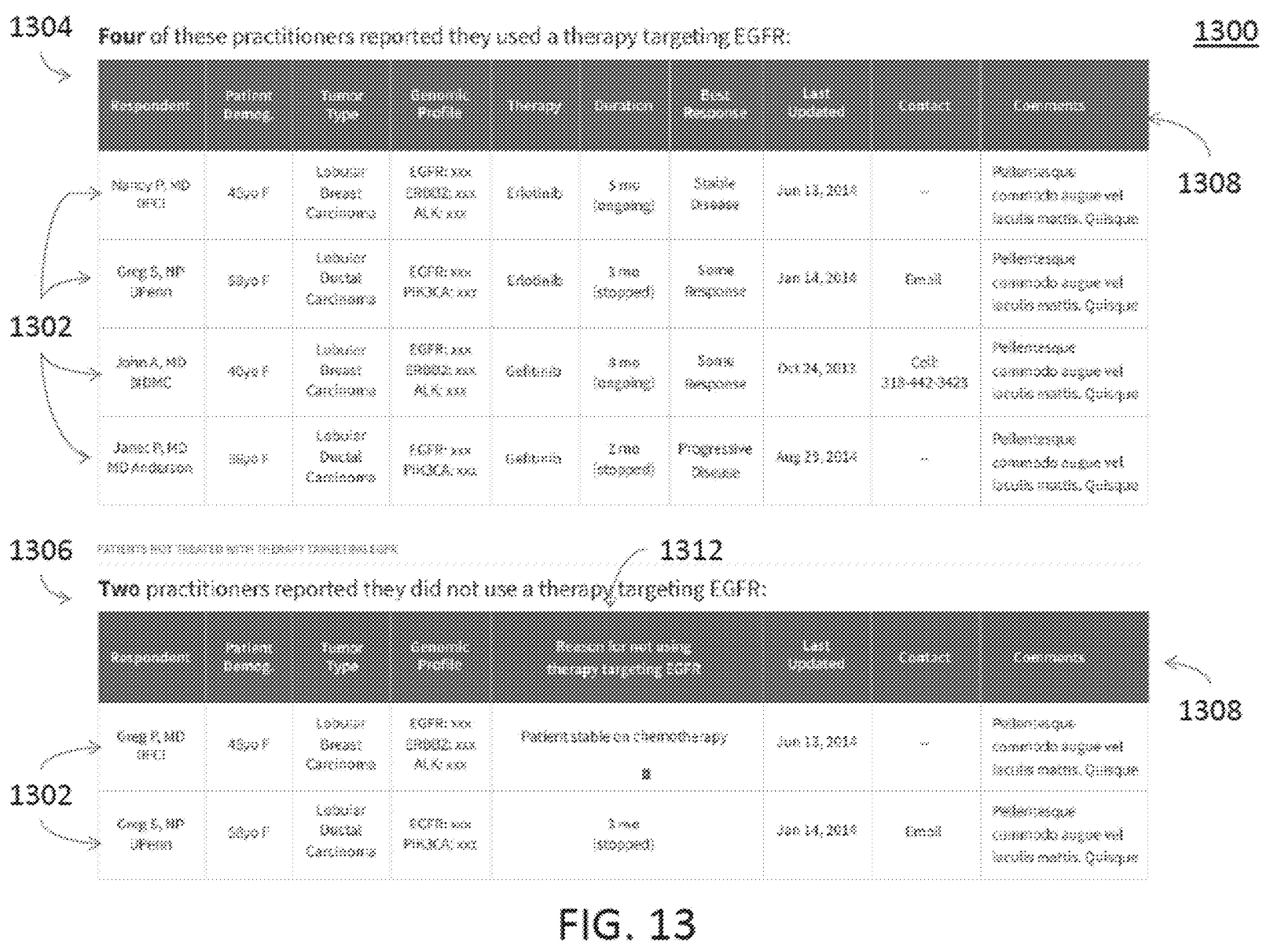

FIG. 13 illustrates one example of a user interface 1300 displaying a compilation of responses to a request. In one embodiment, the compilation includes one or more responses 1302 categorized by a therapy administered by a physician. For example, a first category 1304 can include responses involving therapies targeting a genomic alteration, a second category 1306 can include responses involving abstinence from administering a therapy targeting the genomic alteration, and a third category (not pictured) can include responses involving a clinical trial for the genomic alteration. Each of the first category 1304 and the second category 1306 can be further organized by one or more genomic alteration parameters 1308.

For example, the genomic alteration parameters 1308 can include a name of a respondent, patient demographic information (e.g., a patient's age, gender, etc.), a tumor type (e.g., a type of tumor associated with a patient), a genomic profile (e.g., information about one or more patient genomes), contact information (e.g., contact information for the respondent), update history information (e.g., the last date at which a response's genomic alteration parameters 1308 were modified), and/or a comments section.

According to one embodiment, the first category 1304 further includes therapy information 1310. For example, the therapy information 1310 can include a therapy name, a therapy duration (e.g., a length of time over which a patient underwent the therapy), and/or best response information (e.g., no response, some response, stable disease, etc.).

Furthermore, the second category 1306 can include abstinence information 1312. In some examples, the abstinence information 1312 includes a reason for abstaining from administering a therapy to a patient (e.g., a patient had already become stable from chemotherapy, etc.).

Returning to FIG. 12, in some embodiments, one or more of the genomic alterations 1202 may not have been previously addressed by a physician, or a physician may not respond to a request for information about an indicated genomic alteration 1202. Accordingly, the system notes that a request has not been satisfactorily fulfilled, and in some examples, the system is automatically prompted to send a notification to an originator of the request after a time period (e.g., 24 hours, 48 hours, 72 hours, one week, etc.) has elapsed. The notification can include, for example, additional resource information to address the request, and can include one or more suggested courses of action for the originator of the request to pursue.

Other embodiments of the invention may relate to implementations disclosed and discussed in U.S. application Ser. No. 14/146,743, entitled SYSTEM AND METHOD FOR MANAGING GENOMIC TESTING RESULTS, filed Jan. 3, 2014, which forms an integral part of this specification.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of identifying patient-specific treatment based on genomic information, comprising:
   receiving, by one or more processors, a plurality of genomic alterations;
   generating a plurality of genomic alteration groups by grouping the plurality of genomic alterations based on functional similarities of the plurality of genomic alterations;
   receiving, by the one or more processors, a plurality of disease subtypes;
   generating a plurality of disease ontology groups by grouping the plurality of disease subtypes based on functional similarities of the plurality of disease subtypes;
   receiving, by the one or more processors, data representing a genomic alteration and a disease phenotype associated with a patient;
   generating, based on the data representing the genomic alteration and the disease phenotype associated with the patient, a tuple data structure comprising two elements connected by a relation;
   adding the tuple data structure to a data model comprising a plurality of tuples, wherein the data model comprises a learning model configured to be improved over time;
   determining if there is another patient having the same genomic alteration and the same disease phenotype associated with the patient;
   if there is no patient having the genomic alteration and the same disease phenotype associated with the patient:
      automatically identifying from the generated plurality of genomic alteration groups, by the one or more processors, a pre-defined genomic alteration group comprising the genomic alteration;
      automatically identifying from the generated plurality of disease ontology groups, by the one or more processors, a pre-defined disease ontology group comprising the disease phenotype;
      automatically identifying, by the one or more processors, a plurality of similar patients based on the pre-defined genomic alteration group and the pre-defined disease ontology group;
   displaying, on a display, a selectable data structure corresponding to the genomic alteration, wherein the data structure comprises information related to one or more physicians that provided treatment to the plurality of similar patients;
   receiving a user selection of the data structure; and
   responsive to receiving the user selection,
      providing a user control for sending a request to one of the one or more physicians, and
      identifying a patient-specific treatment for the patient based on the plurality of similar patients.

2. The method of claim 1, wherein the pre-defined genomic alteration group corresponds to a combination of attributes that defines a unique set of gene states.

3. The method of claim 1, wherein the pre-defined disease ontology group comprises a plurality of diseases sharing one or more of: genomic alteration, progression of disease state, treatment, and clinical behavior.

4. The method of claim 1, further comprising ranking the one or more physicians based on successful treatment outcome.

5. The method of claim 1, further comprising displaying the plurality of similar patients.

6. The method of claim 5, wherein the plurality of similar patients is ranked based on outcome information associated with the plurality of similar patients.

7. The method of claim 1, wherein the request comprises a question in a structured format.

8. The method of claim 1, further comprising receiving a response to the request.

9. The method of claim 8, wherein the response comprises structured data, unstructured data, or a combination thereof.

10. The method of claim 1, further comprising:
    displaying a matrix of responses from the one or more physicians.

11. The method of claim 10, wherein the matrix comprises anonymized patient information.

12. The method of claim 1, wherein the one or more physicians are identified based on communication settings associated with the one or more physicians.

13. The method of claim 1, wherein a plurality of disease ontology groups are automatically formed based on a criteria.

14. The method of claim 1, further comprising sending a reminder to a physician of the one or more physicians.

15. The method of claim 1, wherein the model comprises a graph model.

16. The method of claim 15, wherein the graph model is configured to store information organized into a plurality of tuples.

17. The method of claim 15, further comprising determining one or more actionable items within the graph model based on the genomic alteration and the disease phenotype associated with the patient.

18. A system, comprising:
a display;
one or more processors;
a memory; and
one or more programs, wherein the one or more programs are stored in the memory and configured to be executed by the one or more processors, the one or more programs including instructions for:
receiving, by one or more processors, a plurality of genomic alterations;
generating a plurality of genomic alteration groups by grouping the plurality of genomic alterations based on functional similarities of the plurality of genomic alterations;
receiving, by the one or more processors, a plurality of disease subtypes;
generating a plurality of disease ontology groups by grouping the plurality of disease subtypes based on functional similarities of the plurality of disease subtypes;
receiving, by the one or more processors, data representing a genomic alteration and a disease phenotype associated with a patient;
generating, based on the data representing the genomic alteration and the disease phenotype associated with the patient, a tuple data structure comprising two elements connected by a relation;
adding the tuple data structure to a data model comprising a plurality of tuples, wherein the data model comprises a learning model configured to be improved over time;
determining if there is another patient having the same genomic alteration and the same disease phenotype associated with the patient;
if there is no patient having the genomic alteration and the same disease phenotype associated with the patient:
   automatically identifying from the generated plurality of genomic alteration groups, by the one or more processors, a pre-defined genomic alteration group comprising the genomic alteration;
   automatically identifying from the generated plurality of disease ontology groups, by the one or more processors, a pre-defined disease ontology group comprising the disease phenotype;
   automatically identifying, by the one or more processors, a plurality of similar patients based on the pre-defined genomic alteration group and the pre-defined disease ontology group; and
   displaying, on the display, a selectable data structure corresponding to the genomic alteration, wherein the data structure comprises information related to one or more physicians that provided treatment to the plurality of similar patients;
receiving a user selection of the data structure; and
responsive to receiving the user selection,
   providing a user control for sending a request to one of the one or more physicians, and
   identifying a patient-specific treatment for the patient based on the plurality of similar patients.

19. A non-transitory computer-readable storage medium storing one or more programs, the one or more programs comprising instructions, which when executed by one or more processors of one or more electronic devices, cause the one or more electronic devices to:
receive, by one or more processors, a plurality of genomic alterations;
generate a plurality of genomic alteration groups by grouping the plurality of genomic alterations based on functional similarities of the plurality of genomic alterations;
receive, by the one or more processors, a plurality of disease subtypes;
generate a plurality of disease ontology groups by grouping the plurality of disease subtypes based on functional similarities of the plurality of disease subtypes;
receive, by the one or more processors, data representing a genomic alteration and a disease phenotype associated with a patient;
generating, based on the data representing the genomic alteration and the disease phenotype associated with the patient, a tuple data structure comprising two elements connected by a relation;
adding the tuple data structure to a data model comprising a plurality of tuples, wherein the data model comprises a learning model configured to be improved over time;
determining if there is another patient having the same genomic alteration and the same disease phenotype associated with the patient;
if there is no patient having the genomic alteration and the same disease phenotype associated with the patient:
   automatically identify from the generated plurality of genomic alteration groups, by the one or more processors, a pre-defined genomic alteration group comprising the genomic alteration;
   automatically identify from the generated plurality of disease ontology groups, by the one or more processors, a pre-defined disease ontology group comprising the disease phenotype;
   automatically identify, by the one or more processors, a plurality of similar patients based on the pre-defined genomic alteration group and the pre-defined disease ontology group; and
display, on a display associated with an electronic device of the one or more electronic devices, a selectable data structure corresponding to the genomic alteration, wherein the data structure comprises information related to one or more physicians that provided treatment to the plurality of similar patients;
receive a user selection of the data structure; and
responsive to receiving the user selection,
provide a user control for sending a request to one of the one or more physicians, and
identify a patient-specific treatment for the patient based on the plurality of similar patients.

* * * * *